US011628021B2

(12) United States Patent
Chaplin et al.

(10) Patent No.: US 11,628,021 B2
(45) Date of Patent: Apr. 18, 2023

(54) INSTRUMENT INTERFACE FOR ROBOTIC SURGICAL INSTRUMENT

(71) Applicant: CMR Surgical Limited, Cambridge (GB)

(72) Inventors: Ben Robert Chaplin, Cambridge (GB); Brendan Haig Baylis, Cambridge (GB)

(73) Assignee: CMR Surgical Limited, Cambridge (GB)

( * ) Notice: Subject to any disclaimer, the term of this patent is extended or adjusted under 35 U.S.C. 154(b) by 437 days.

(21) Appl. No.: 16/620,329

(22) PCT Filed: Jun. 6, 2018

(86) PCT No.: PCT/GB2018/051544
§ 371 (c)(1),
(2) Date: Dec. 6, 2019

(87) PCT Pub. No.: WO2018/224827
PCT Pub. Date: Dec. 13, 2018

(65) Prior Publication Data
US 2020/0188040 A1 Jun. 18, 2020

(30) Foreign Application Priority Data

Jun. 6, 2017 (GB) ..................................... 1709016
Jun. 6, 2017 (GB) ..................................... 1709017
(Continued)

(51) Int. Cl.
*A61B 34/30* (2016.01)
*A61B 34/00* (2016.01)
(Continued)

(52) U.S. Cl.
CPC .............. *A61B 34/30* (2016.02); *A61B 17/29* (2013.01); *A61B 34/71* (2016.02); *B25J 9/0009* (2013.01);
(Continued)

(58) Field of Classification Search
CPC ......... A61B 34/30; A61B 17/29; A61B 34/71; A61B 2017/00477; A61B 2017/2927;
(Continued)

(56) References Cited

U.S. PATENT DOCUMENTS 7,169,141 B2   1/2007   Brock et al.
2010/0163057 A1*  7/2010   Anderson .............. A61B 34/71
                                                   606/130
(Continued)

FOREIGN PATENT DOCUMENTS

CN   102046081 A   5/2011
CN   105662588 A   6/2016
(Continued)

OTHER PUBLICATIONS

Notification of Reasons for Refusal dated Dec. 9, 2021, for related Japanese Patent Application No. 2019-567373.
(Continued)

*Primary Examiner* — Gary Jackson
*Assistant Examiner* — Sebastian X Lukjan
(74) *Attorney, Agent, or Firm* — Renner, Otto, Boisselle & Sklar, LLP

(57) ABSTRACT

A robotic surgical instrument, comprising: a shaft; an end effector element; an articulation at a distal end of the shaft for articulating the end effector element, the articulation comprising a first joint permitting the end effector to adopt a range of configurations relative to the longitudinal axis of the shaft, the first joint being driveable by a first pair of driving elements; and an instrument interface at a proximal
(Continued)

end of the shaft, comprising: a chassis formed from the securement of a first chassis portion to a second chassis portion, wherein the first pair of driving elements are secured relative to the chassis, the chassis portions being configured to be secured together by sliding the chassis portions relative to each other in a longitudinal direction parallel to the longitudinal axis of the shaft.

17 Claims, 17 Drawing Sheets

(30) Foreign Application Priority Data

Aug. 24, 2017 (GB) ...................................... 1713625
Feb. 7, 2018 (GB) ...................................... 1802018

(51) Int. Cl.
*A61B 17/29* (2006.01)
*B25J 9/10* (2006.01)
*B25J 15/00* (2006.01)
*B25J 17/02* (2006.01)
*B25J 9/00* (2006.01)
*A61B 17/00* (2006.01)

(52) U.S. Cl.
CPC ............. *B25J 9/104* (2013.01); *B25J 9/1045* (2013.01); *B25J 15/0028* (2013.01); *B25J 17/02* (2013.01); *B25J 17/0283* (2013.01); *A61B 2017/00477* (2013.01); *A61B 2017/2927* (2013.01); *A61B 2017/2929* (2013.01); *A61B 2017/2932* (2013.01); *A61B 2017/2938* (2013.01); *A61B 2034/302* (2016.02); *A61B 2034/305* (2016.02); *A61B 2034/306* (2016.02); *A61B 2034/715* (2016.02)

(58) Field of Classification Search
CPC .... A61B 2017/2929; A61B 2017/2932; A61B 2034/302; A61B 2034/305; A61B 2034/306; A61B 2034/715; B25J 9/0009; B25J 9/104; B25J 9/1045; B25J 15/00028; B25J 17/02; B25J 17/0283
See application file for complete search history.

(56) References Cited

U.S. PATENT DOCUMENTS

| 2012/0165828 | A1 | 6/2012 | Duque et al. |
| 2014/0276776 | A1 | 9/2014 | Parihar et al. |
| 2017/0086823 | A1* | 3/2017 | Leimbach ............ A61B 17/068 |

FOREIGN PATENT DOCUMENTS

| CN | 105997250 A | 10/2016 |
| JP | 2013215505 A | 10/2013 |
| WO | 2013/063522 | 5/2013 |
| WO | 2017013943 A1 | 1/2017 |

OTHER PUBLICATIONS

Search Report issued in corresponding GB Patent Application No. 1802018.0, dated Jul. 20, 2018.
International Search Report issued in corresponding International Patent Application No. PCT/GB2018/051541, dated Jun. 8, 2018.
First Office Action dated Sep. 5, 2022, for corresponding Chinese Patent Application No. 201880038004.5.

* cited by examiner

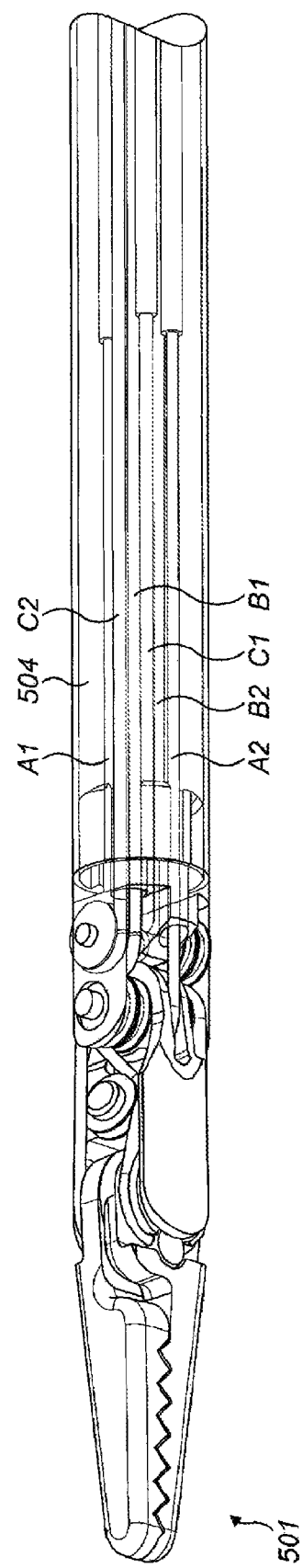

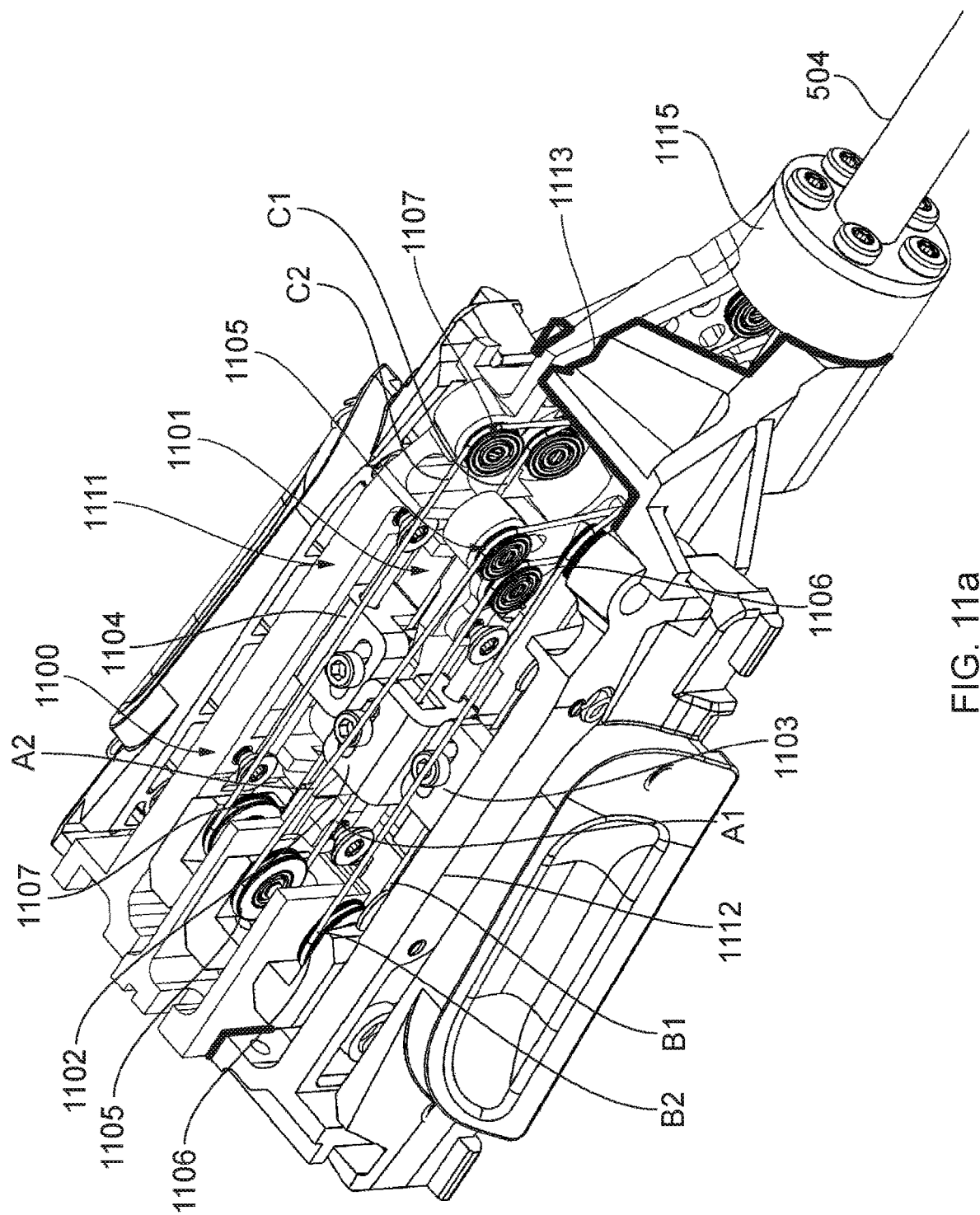

INSTRUMENT INTERFACE FOR ROBOTIC SURGICAL INSTRUMENT

FIELD

This invention relates to a robotic surgical instrument having an instrument interface comprising a first and second chassis portions secured together.

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 to access the surgical site. At its distal end, the instrument comprises an end effector 106 for engaging in a medical procedure.

FIG. 2 illustrates a typical surgical instrument 200 for performing robotic laparoscopic surgery. The surgical instrument comprises a base 201 by means of which the surgical instrument connects to the robot arm. A shaft 202 extends between base 201 and articulation 203. Articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

FIG. 3 illustrates an example of a known surgical instrument 300 in which end effector 204 is permitted to move relative to shaft 202 by means of pitch joint 301 and two yaw joints 302. Joint 301 enables the end effector 204 to rotate about pitch axis 303. Joints 302 enable each jaw of the end effector 204 to rotate about yaw axis 304. The joints are driven by cables 306, 307 and 308. Pulley 305 is used to direct cables 307 and 308 from their passage over the pitch joint to the yaw joints. Pulley 305 is offset from the central axis of the articulation 203.

In a typical laparoscopy operation, a surgeon utilises many instruments, and hence exchanges one instrument for another many times. It is therefore desirable to minimise the time taken and maximise the ease with which one instrument is detached from a robot arm and a different instrument is attached. Additionally, it is desirable to minimise the time taken in setting up the instrument ready for use once it has been attached to the robot arm.

As such, the surgical instrument 300 may be attached at its proximal end to the distal end of the robotic arm by an instrument interface. The instrument interface may connect, or engage with, an interface of the robotic arm. Mechanical drive to drive the joints of the instrument (e.g. joints 301 and 302) may be transferred to the instrument from the robotic arm via the robotic arm interface and the instrument interface.

SUMMARY

According to the present invention there is provided a robotic surgical instrument, comprising: a shaft; an end effector element; an articulation at a distal end of the shaft for articulating the end effector element, the articulation comprising a first joint permitting the end effector to adopt a range of configurations relative to the longitudinal axis of the shaft, the first joint being driveable by a first pair of driving elements; and an instrument interface at a proximal end of the shaft, comprising: a chassis formed from the securement of a first chassis portion to a second chassis portion, wherein the first pair of driving elements are secured relative to the chassis, the chassis portions being configured to be secured together by sliding the chassis portions relative to each other in a longitudinal direction parallel to the longitudinal axis of the shaft.

The chassis may comprise a securing mechanism operable to secure the first chassis portion to the second chassis portion when the chassis portions are slid relative to each other in the longitudinal direction.

The chassis portions may be configured to be secured together by sliding the chassis portions relative to each other in the longitudinal direction from a first position in which the securing mechanism is disengaged, to a second position in which the securing mechanism is engaged to secure the chassis portions to each other.

The securing mechanism may comprise securing elements configured to engage when the chassis portions are slid towards each other in the longitudinal direction to thereby secure the chassis portions together.

The first chassis portion may comprise a mounting block to which the proximal end of the shaft is mounted.

The chassis portions may be configured to be secured together by sliding the chassis portions relative to each other to bring the second chassis portion towards the proximal end of the shaft.

The chassis portions may be mutually configured to prevent further sliding of the second chassis portion relative to the first chassis portion towards the proximal end of the shaft when the chassis portions are secured together.

The instrument interface may further comprise a first set of pulleys about which the first pair of driving elements are constrained to move, the first set of pulleys being rotatably secured to the second chassis portion so that tension in the first pair of driving elements holds the second chassis portion against the first chassis portion in the longitudinal direction when the chassis portions are secured together.

The chassis portions may be configured so that a part of the second chassis portion abuts against a part of the first chassis portion when the chassis portions are secured together to prevent further sliding of the second chassis portion relative to the first chassis portion in the longitudinal direction towards the proximal end of the shaft, the tension in the first pair of driving elements holding the part of the second chassis portion against the part of the first chassis portion.

The part of the first chassis portion may be a mating surface against which the second chassis portion abuts when the chassis portions are secured together.

The mating surface may be transverse to the longitudinal direction.

The mating surface may be integral with the mounting block.

The first chassis portion and the second chassis portion may each comprise a lateral interfacing surface, and the chassis portions may be configured to be secured together by laterally engaging the chassis portions by bringing the chassis portions together along a lateral direction so that the lateral interface surface of the first chassis portion interfaces the lateral interface surface of the second chassis portion, and thereafter sliding the chassis portions relative to each other in a longitudinal direction parallel to the longitudinal axis of the shaft.

The securing mechanism may comprise a set of one or more protrusions located on a distal end of the second chassis portion and a corresponding set of one or more recesses located on the mating surface, and the chassis may be arranged so that the protrusions mate into the recesses when the second chassis portion is slid relative to the first chassis portion along the longitudinal direction.

The securing mechanism may comprise a first latch part located on the first chassis portion and a second latch part on the second chassis portion, the chassis being arranged so that the first latch part and the second latch part engage when the chassis portions are slid relative to the first chassis portion along the longitudinal direction.

The securing mechanism may comprise a lug located at the proximal end of the first chassis portion and an opening located at the proximal end of the second chassis portion, wherein the lug is configured to extend into the opening when the chassis portions are slid relative to the first chassis portion along the longitudinal direction.

The first pair of driving elements may be cables.

BRIEF DESCRIPTION OF DRAWINGS

The present invention will now be described by way of example with reference to the accompanying drawings. In the drawings:

FIG. 8 shows arrangements of driving elements in an instrument shaft;

FIGS. 11a and 11b show a top-side and bottom-side view respectively of the instrument interface;

DETAILED DESCRIPTION

Figure 1:
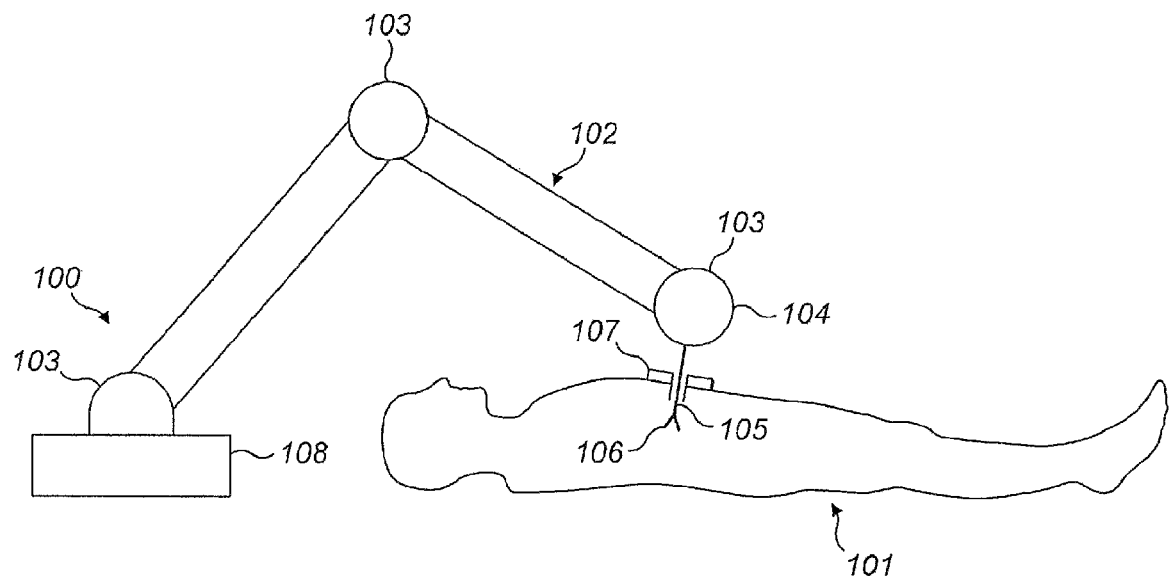
FIG. 1 shows a surgical robot performing a surgical procedure.

The present disclosure is directed to a surgical robotic instrument having an instrument interface at its proximal end comprising a chassis. The instrument further comprises an instrument shaft and an end effector element attached to the distal end of the shaft. An articulation at the distal end of the shaft can articulate the end effector element relative to the shaft. The proximal end of the instrument shaft is mounted to the chassis. Driving elements (e.g. cables) extend from the instrument interface through the shaft to the articulation for driving joints of the articulation to thereby articulate the end effector element.

The chassis is formed of two parts: a first chassis portion and a second chassis portion. The two chassis portions are secured together to form the chassis. Forming the chassis by securing two chassis portions together may aid the assembly of the instrument interface by enabling at least some of the driving elements (and associated pulleys about which the driving elements are constrained to move) to be secured in place prior to the chassis being assembled. To assemble the chassis, the two chassis portions are slid relative to each other in a longitudinal direction parallel to the longitudinal axis of the shaft. The chassis portions may be slid relative to each other from a first position (in which they are not secured together) to a second position (in which they are secured together). The chassis portions may be laterally engaged in the first position; i.e. the chassis portions may be configured to be secured together by laterally engaging the chassis portions and thereafter sliding the chassis portions relative to each other in the longitudinal direction. To place the chassis portions in the first position, the chassis portions may first be brought together along a lateral direction. The lateral direction is substantially transverse to the longitudinal direction of the instrument shaft. The two chassis portions are brought together so that in the first position the two chassis portions are offset relative to each other along the longitudinal direction of the shaft. The two chassis portions are then slid relative to each other in a direction parallel, or substantially parallel to, the longitudinal direction of the shaft to secure the portions together. In other words, the two chassis portions are secured together by slideably engaging the portions, i.e. the two chassis portions slideably engage each other to secure the portions together.

The chassis comprises a securing mechanism that operates to secure the two chassis portions together when the chassis portions are slid relative to each other in the longitudinal direction. That is, the act of sliding the chassis portions relative to each other along the longitudinal direction of the shaft activates, or engages the securing mechanism to thereby secure the chassis portions together. Thus, the chassis portions may be slideable relative to each other in a longitudinal direction parallel to the axial direction of the shaft from a first position in which the chassis portions are laterally engaged and the securing mechanism disengaged, to a second position in which the securing mechanism is engaged to secure the chassis portions to each other.

It has been appreciated that assembling the chassis by sliding the two chassis portions relative to each other in the longitudinal direction means that the tension in the driving elements (which extend from the chassis to the articulation at the distal end of the shaft) conveniently functions to hold the chassis portions in place in the longitudinal direction. In other words, the tension in the driving elements can be utilised to enhance the stability of the assembled chassis. This will be explained in more detail below with reference to the described examples.

Figure 4:
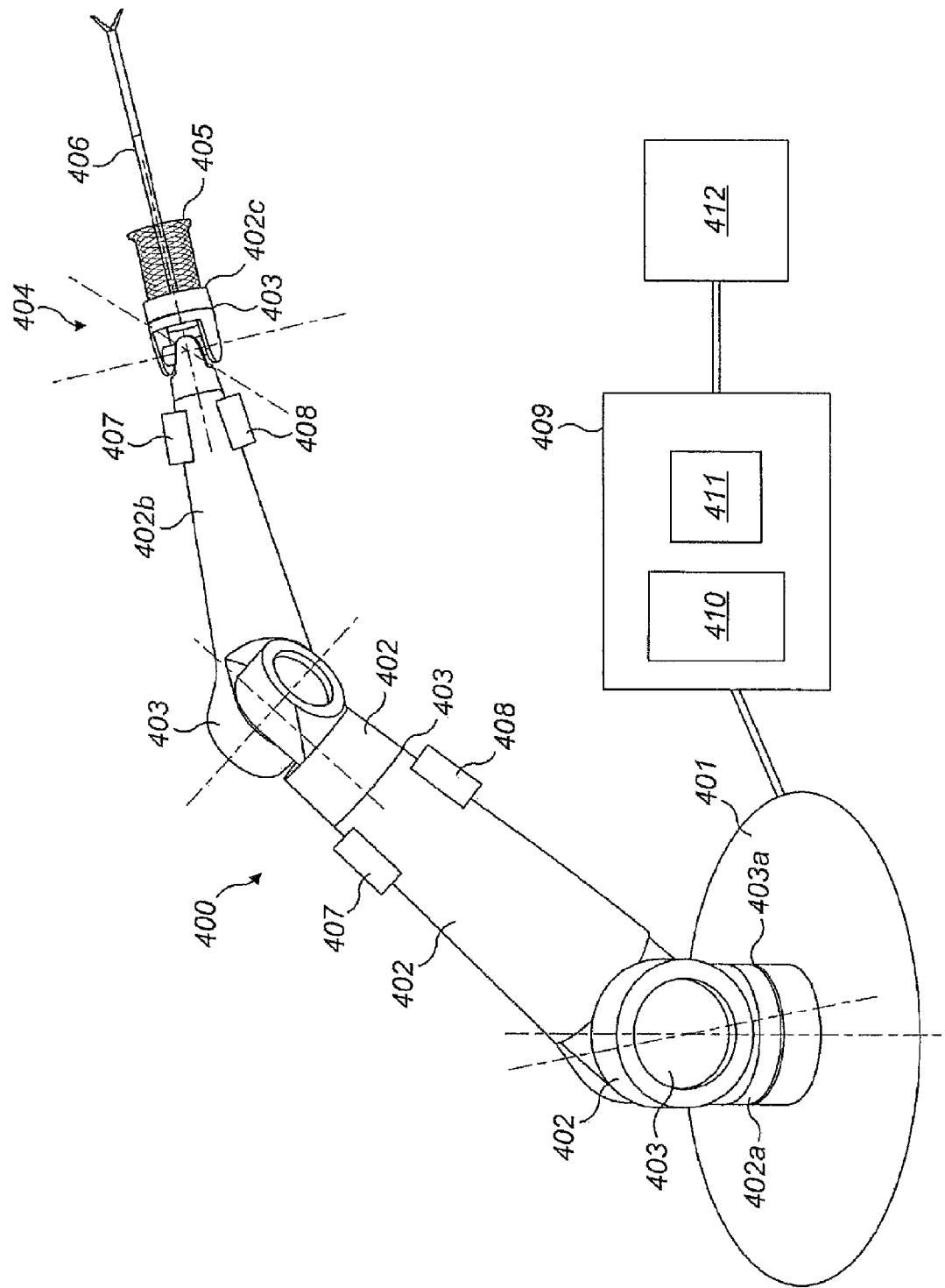
FIG. 4 shows a surgical robot.

FIG. 4 illustrates a surgical robot having an arm 400 which extends from a base 401. The arm comprises a number of rigid limbs 402. The limbs are coupled by revolute joints 403. The most proximal limb 402a is coupled to the base by joint 403*a*. It and the other limbs are coupled in series by further ones of the joints 403. A wrist 404 is made up of four individual revolute joints. The wrist 404 couples one limb (402*b*) to the most distal limb (402*c*) of the arm. The most distal limb 402*c* carries an attachment 405 for a surgical instrument 406. Each joint 403 of the arm has one or more motors 407 which can be operated to cause rotational motion at the respective joint, and one or more position and/or torque sensors 408 which provide information regarding the current configuration and/or load at that joint. The motors may be arranged proximally of the joints whose motion they drive, so as to improve weight distribution. For clarity, only some of the motors and sensors are shown in FIG. 4. The arm may be generally as described in our co-pending patent application PCT/GB2014/053523.

Figure 2:
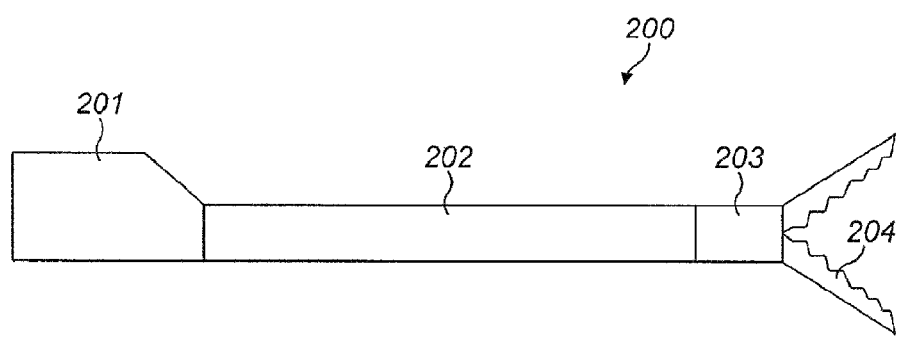
FIG. 2 shows a known surgical instrument.
Figure 3:
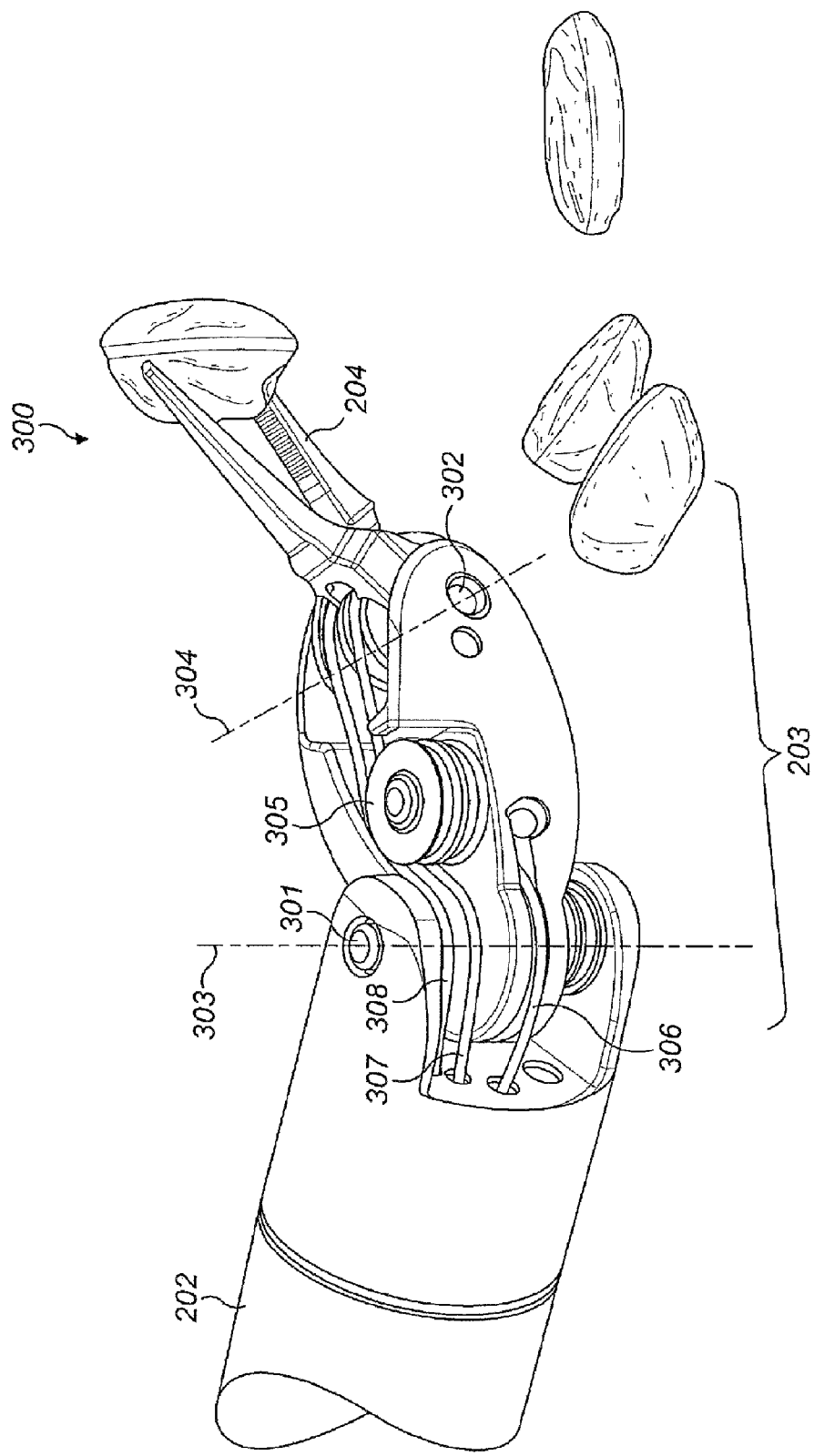
FIG. 3 shows a known arrangement of an articulated end effector of a surgical instrument.

The arm terminates in an attachment 405 for interfacing with the instrument 406. The instrument 406 may take the form described with respect to FIG. 2. The attachment 405 comprises a drive assembly for driving articulation of the instrument, and a drive assembly interface for engaging an instrument interface of the instrument 406. Movable interface elements of the drive assembly interface mechanically engage corresponding movable interface elements of the instrument interface in order to transfer drive from the robot arm to the instrument. One instrument may be exchanged for another several times during a typical operation. Thus, the instrument is attachable and detachable from the robot arm during the operation. Features of the drive assembly interface and the instrument interface may aid their alignment when brought into engagement with each other, so as to reduce the accuracy with which they need to be aligned by the user.

The instrument 406 comprises an end effector for performing an operation. The end effector may take any suitable form. The end effector may comprise one or more end effector elements. For example, the end effector elements may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation may comprise one or more joints which permit the end effector to move relative to the shaft of the instrument. The one or more joints in the articulation are actuated by driving elements, such as cables. These driving elements are secured at the other end of the instrument shaft to the interface elements of the instrument interface. The driving elements therefore extend from the instrument interface to the joints of the articulation through the instrument shaft. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed with the robot arm. The controllers are connected via a communication bus to control unit 409. A control unit 409 comprises a processor 410 and a memory 411. Memory 411 stores in a non-transient way software that is executable by the processor to control the operation of the motors 407 to cause the arm 400 to operate in the manner described herein. In particular, the software can control the processor 410 to cause the motors (for example via distributed controllers) to drive in dependence on inputs from the sensors 408 and from a surgeon command interface 412. The control unit 409 is coupled to the motors 407 for driving them in accordance with outputs generated by execution of the software. The control unit 409 is coupled to the sensors 408 for receiving sensed input from the sensors, and to the command interface 412 for receiving input from it. The respective couplings may, for example, each be electrical or optical cables, or may be provided by a wireless connection. The command interface 412 comprises one or more input devices whereby a user can request motion of the end effector in a desired way. The input devices could, for example, be manually operable mechanical input devices such as control handles or joysticks, or contactless input devices such as optical gesture sensors. The software stored in memory 411 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, a surgeon at the command interface 412 can control the instrument 406 to move in such a way as to perform a desired surgical procedure. The control unit 409 and/or the command interface 412 may be remote from the arm 400.

Figures 5A, 5B:
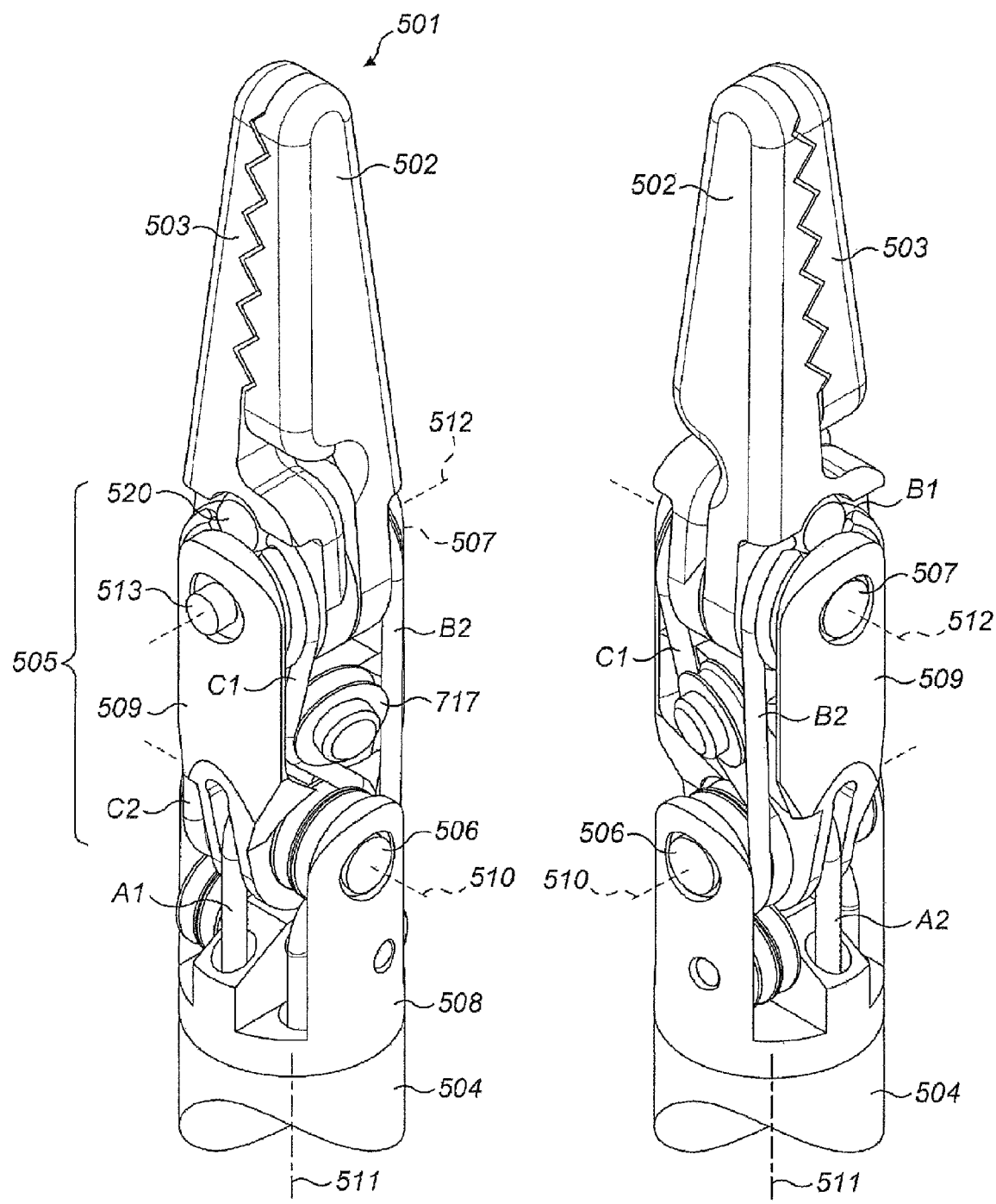
FIGS. 5a and 5b show a distal end of a surgical instrument.

FIGS. 5*a* and 5*b* illustrate opposing views of the distal end of an example surgical instrument. In FIGS. 5*a* and 5*b*, the end effector 501 comprises a pair of end effector elements 502, 503, which in this example are depicted as a pair of opposing serrated jaws. It will be understood that this is for illustrative purposes only. The end effector may take any suitably form, such as those described above. The end effector 501 is connected to the instrument shaft 504 by articulation 505. Articulation 505 comprises joints which permit the end effector 501 to move relative to the shaft 504. In this example, the articulation 505 comprises three joints. A first joint 506 permits the end effector 501 to rotate about a first axis 510. The first axis 510 is transverse to the longitudinal axis of the shaft 511. The first joint 506 is arranged so that the shaft 504 terminates at its distal end in the joint 506. A second joint 507 permits the first end effector element 502 to rotate about a second axis 512. The second axis 512 is transverse to the first axis 510. A third joint 513 permits the second end effector element 503 to rotate about the second axis 512.

The first end effector element 502 and the second end effector element 503 may be independently rotatable about the second axis 512 by the second and third joints. The end effector elements may be rotated in the same direction or different directions by the second and third joints. The first end effector element 502 may be rotated about the second axis, whilst the second end effector element 503 is not rotated about the second axis. The second end effector element 503 may be rotated about the second axis, whilst the first end effector element 502 is not rotated about the second axis.

FIGS. 5*a* and 5*b* depict a straight configuration of the surgical instrument in which the end effector is aligned with the shaft 504. In this orientation, the longitudinal axis of the shaft 511 is coincident with the longitudinal axis of the articulation and the longitudinal axis of the end effector. Articulation of the first, second and third joints enables the end effector to take a range of attitudes (i.e. configurations) relative to the shaft.

The articulation 505 comprises a supporting body 509. At one end, the supporting body 509 is connected to the shaft 504 by the first joint 506. At its other end, the supporting body 509 is connected to the end effector 501 by second joint 507 and third joint 513. Thus, first joint 506 permits the supporting body 509 to rotate relative to the shaft 504 about the first axis 510; and the second joint 507 and third joint 513 permit the end effector elements 502, 503 to rotate relative to the supporting body 509 about the second axis 512.

The joints of the articulation 505 are driven by driving elements. The driving elements are elongate elements which extend from the joints in the articulation through the shaft 504 to the instrument interface. Each driving element may be capable of being flexed laterally to its main extent at least in those regions where it engages the internal components of the articulation and instrument interface. In other words, each driving element can be flexed transverse to its longitudinal axis in the specified regions. This flexibility enables the driving elements to wrap around the internal structure of the instrument, such as the joints and pulleys. The driving elements may be wholly flexible transverse to their longitudinal axes. The driving elements may be inflexible along their main extents. The driving elements may resist compression and tension forces applied along their length. In other words, the driving elements may resist compression and tension forces acting in the direction of their longitudinal axes. The driving elements may have a high modulus. The driving elements may remain taut in operation; they may be not permitted to become slack. Thus, the driving elements are able to transfer drive from the instrument interface to the joints. Examples of driving elements include, for example, cables, cords, wires, or ties.

Each joint may be driven by a respective pair of driving elements. Referring to FIGS. 5a and 5b, the first joint 506 is driven by a first pair of driving elements A1,A2. The second joint 507 is driven by a second pair of driving elements B1,B2. The third joint is driven by a third pair of driving elements C1,C2. Each joint of instrument 501 is therefore driven by its own pair of driving elements. In other words, each joint is driven by a dedicated pair of driving elements. The joints may be independently driven. A pair of driving elements may be constructed as a single piece as shown for the third pair of driving elements in FIGS. 5a and 5b. In this case, the single piece is secured to the joint at one point. For example, the third pair of driving elements C1,C2 comprises a ball feature 520 which is secured to the third joint 513. This ensures that when the pair of driving elements is driven, the drive is transferred to motion of the joint about its axis. Alternatively, a pair of driving elements may be constructed as two pieces. In this case, each separate piece is secured to the joint.

Figure 6:
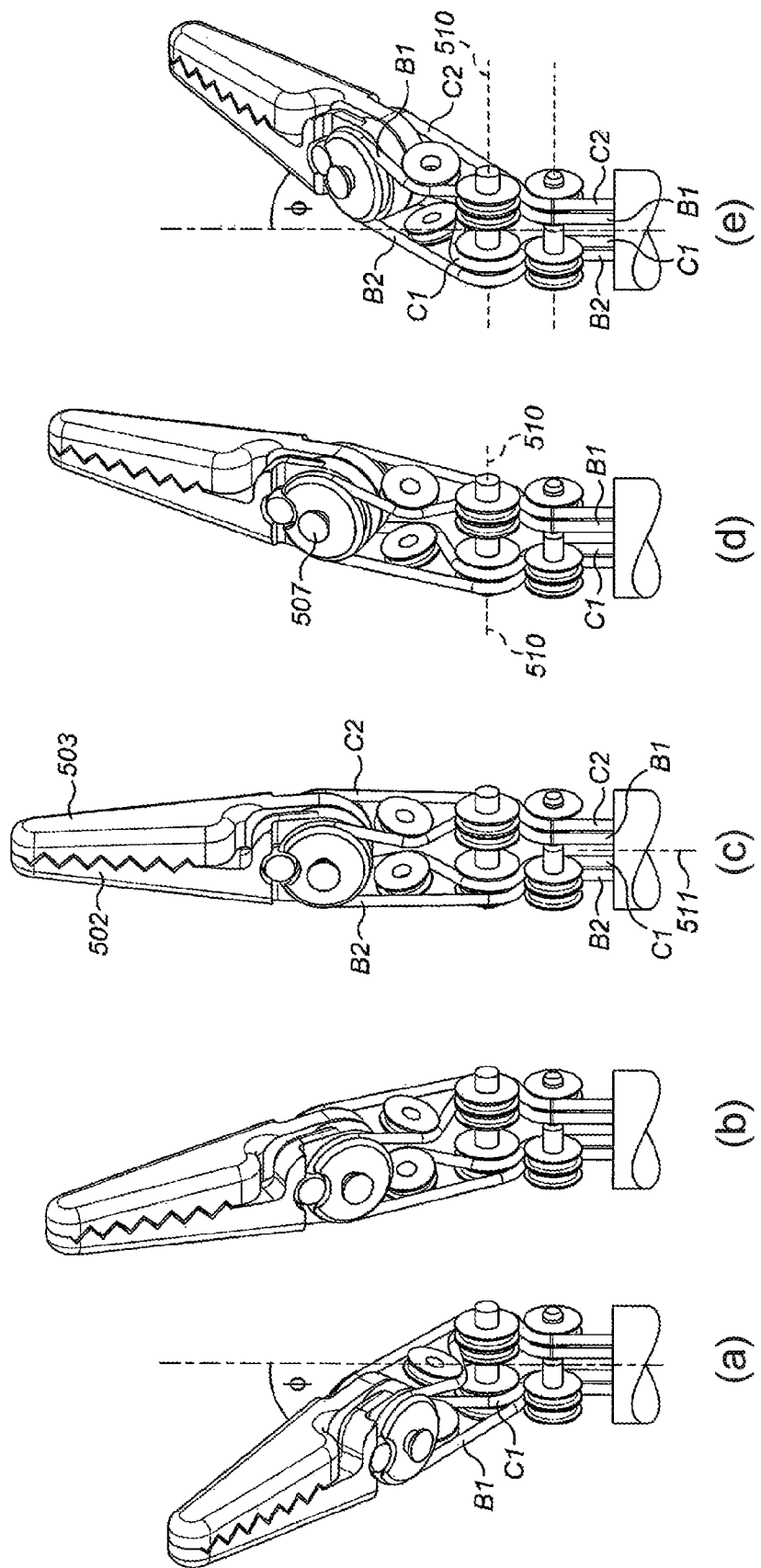
FIG. 6 shows a pulley arrangement of the distal end of the surgical instrument of FIGS. 5a and 5b in a variety of configurations.

FIG. 6 illustrates the distal end of the surgical instrument in five different configurations. Configuration (c) is the straight configuration previously mentioned, in which the end effector is aligned with the instrument shaft. In configurations (a), (b), (d) and (e), rotation about the first joint has occurred relative to configuration (c). In configurations (a), (b), (d) and (e), no rotation about either the second or third joint has occurred relative to configuration (c). Starting from configuration (c), the driving element A2 (not shown) is pulled in order to cause the rotation about the first axis 510 leading to the arrangement of configuration (b). The driving element A2 is further pulled to cause further rotation about the first axis 510 to lead to the arrangement of configuration (a). Starting from configuration (c), the driving element A1 (not shown) is pulled in order to cause rotation about the first axis 510 in an opposing direction to that in configurations (a) and (b), thereby leading to the arrangement of configuration (d). The driving element A1 is further pulled to cause further rotation about the first axis 510 to lead to the arrangement of configuration (e).

Rotation of the end effector 501 about the first axis 510 is bounded by the maximum travel of the first pair of driving elements A1,A2 about the first joint 506. Configuration (a) shows the end effector 501 at maximum rotation about the first axis 510 in one direction, and configuration (e) shows the end effector 501 at maximum rotation about the first axis 510 in the opposing direction. The maximum rotation angle relative to the longitudinal axis of the shaft 511 in both configurations is the angle φ.

Figure 7:
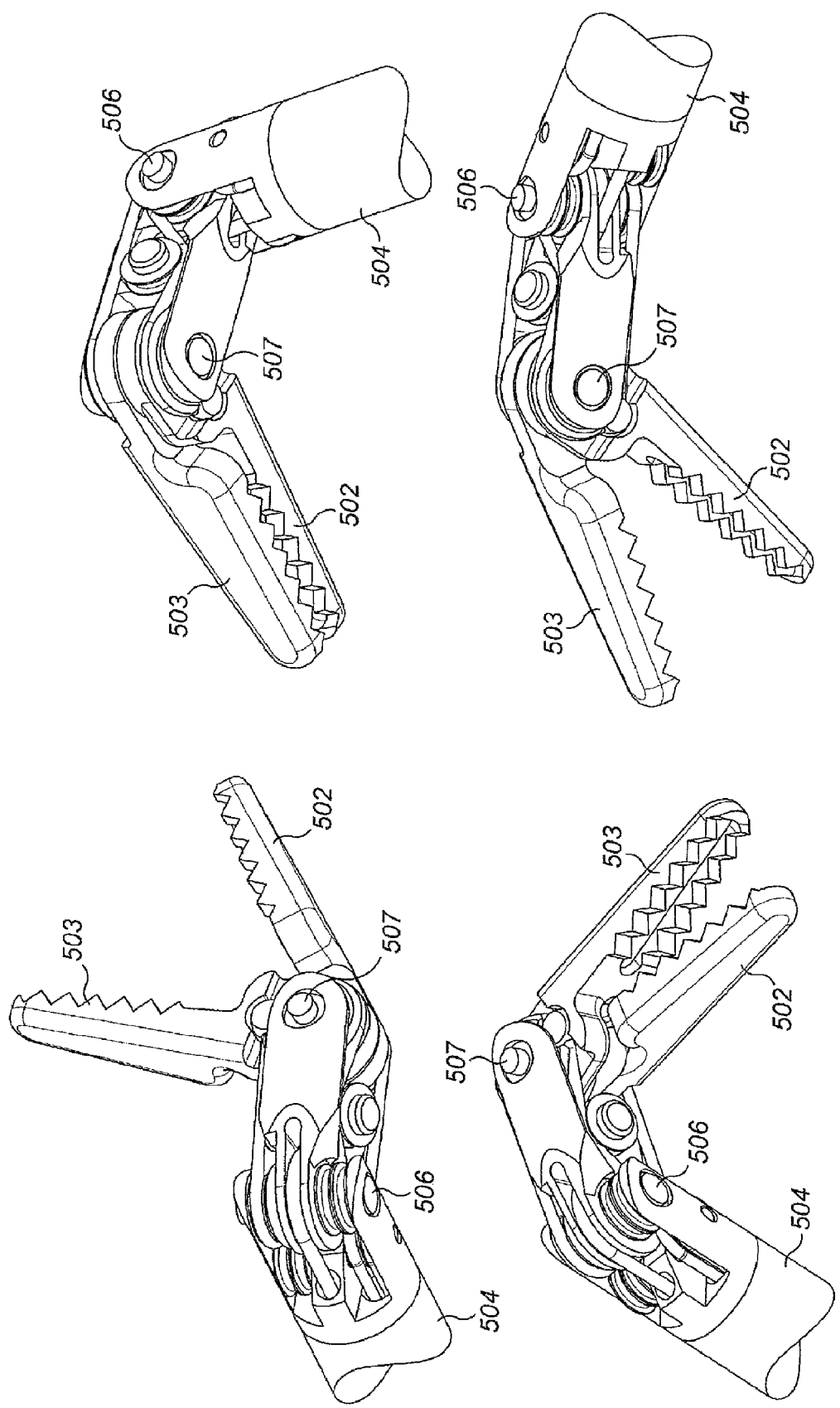
FIG. 7 shows the distal end of the surgical instrument in a variety of non-straight configurations.

FIG. 7 illustrates some further configurations of the distal end of the instrument in which articulation about all the first, second and third joints has been driven relative to the straight configuration of FIGS. 5a and 5b.

As mentioned above, the first, second and third pairs of driving elements A1,A2, B1,B2, C1,C2 extend through the instrument shaft from the distal end of the shaft 504 connected to the articulation to the proximal end of the shaft connected to a drive mechanism of the instrument interface. FIG. 8 illustrates the three pairs of driving elements extending through the instrument shaft 504.

Figure 9A:
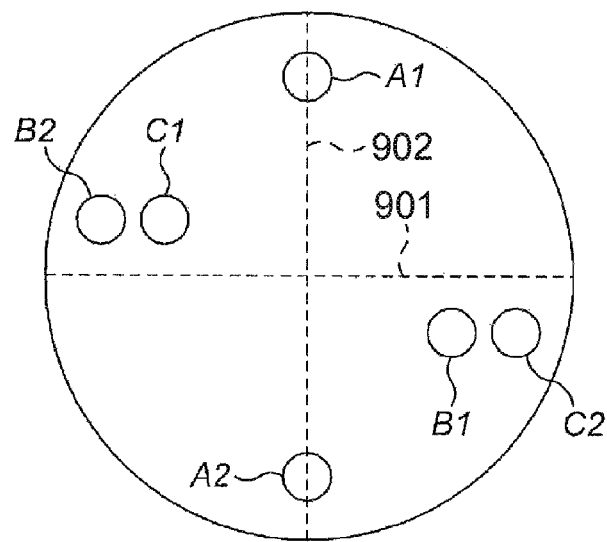
FIGS. 9a and 9b show two cross-sectional views of the instrument shaft showing the position of the driving elements within the shaft.
Figure 9B:
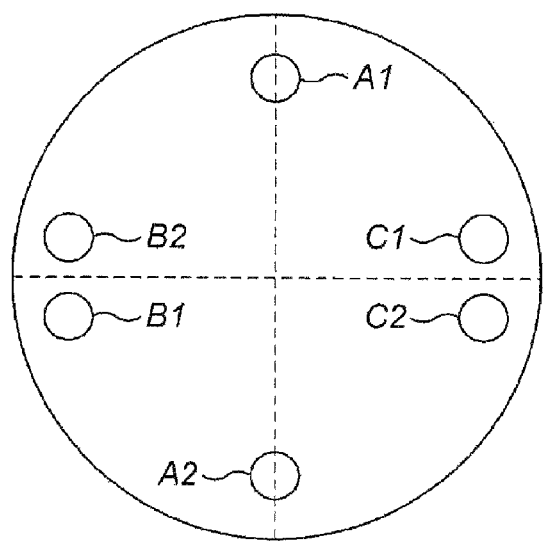

FIGS. 9a and 9b illustrate cross-sections of the shaft depicting the positions of the driving elements.

Configuration (a) of FIG. 9 shows a cross-section of the shaft at the distal end of the shaft. The driving elements A1 and A2 are at opposing sides of the shaft after having left the first joint 506. The driving elements C1 and B2 are adjacent each other on an opposing side of the shaft to the driving elements B1 and C2 which are also adjacent each other. The driving elements C1 and B2 are offset from the driving elements B1 and C2 about an axis 901 which is transverse to the axis 902 connecting driving elements A1 and A2. This is a result of the offset axes of the two pulleys of the second set of pulleys.

Configuration (b) of FIG. 9 shows a cross-section of the shaft at the proximal end of the shaft. In other words, configuration (b) shows the positions of the driving elements as they are about to exit the shaft into the instrument interface. The first pair of driving elements A1 and A2 are on opposing sides of the shaft in a similar arrangement to their arrangement in configuration (a). The first pair of driving elements may be closer together, by virtue of them having moved slightly towards each other over the course of their extent through the shaft. In configuration (b), driving element B1 is located on an opposing side of the shaft to its location in configuration (a). In configuration (b), driving element C1 is located on an opposing side of the shaft to its location in configuration (a). To achieve this, driving element B1 and driving element C1 have not extended down the shaft parallel to the longitudinal axis of the shaft 511. Instead, driving element B1 and driving element C1 have overlapped each other during their extent in the shaft. Driving element B2 has moved a little in the shaft, but remained on the same side of the shaft as in configuration (a), so as to emerge at the proximal end of the shaft adjacent to driving element B1. Driving element C2 has moved a little in the shaft, but remained on the same side of the shaft as in configuration (a), so as to emerge at the proximal end of the shaft adjacent to driving element C1.

It can be seen from FIGS. 9a and 9b that the first pair of driving elements A1,A2 run parallel to the longitudinal direction of the shaft. Moreover, the first pair of driving elements lie on a central plane of the instrument shaft. The central plane bifurcates the instrument shaft along its length.

Figure 10A:
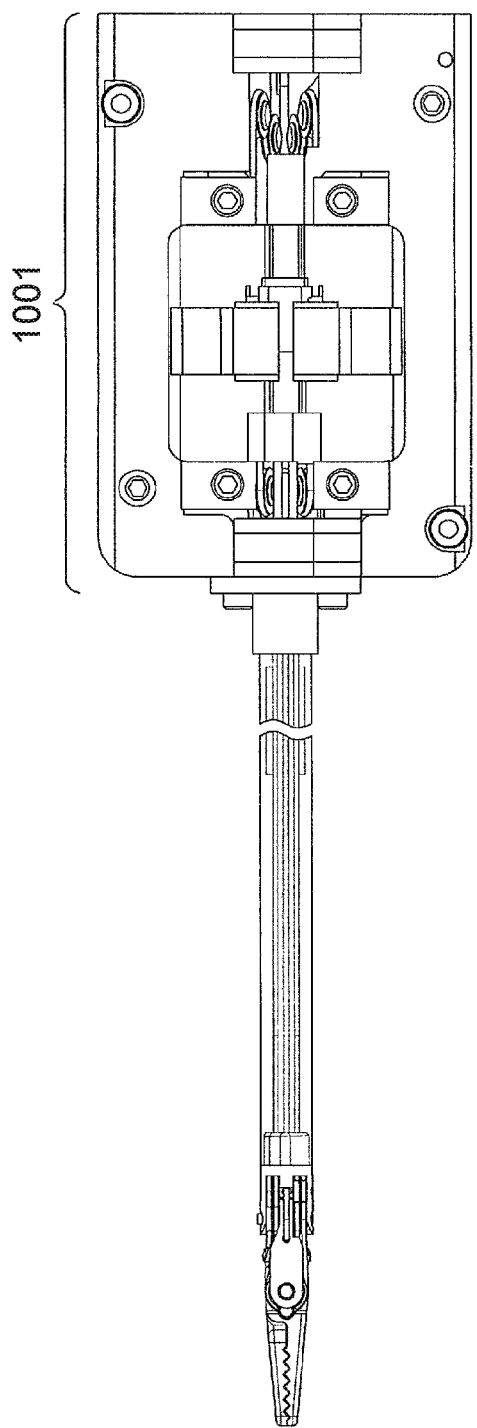
FIGS. 10a and 10b show two views of a surgical instrument including an instrument interface.
Figure 10B:
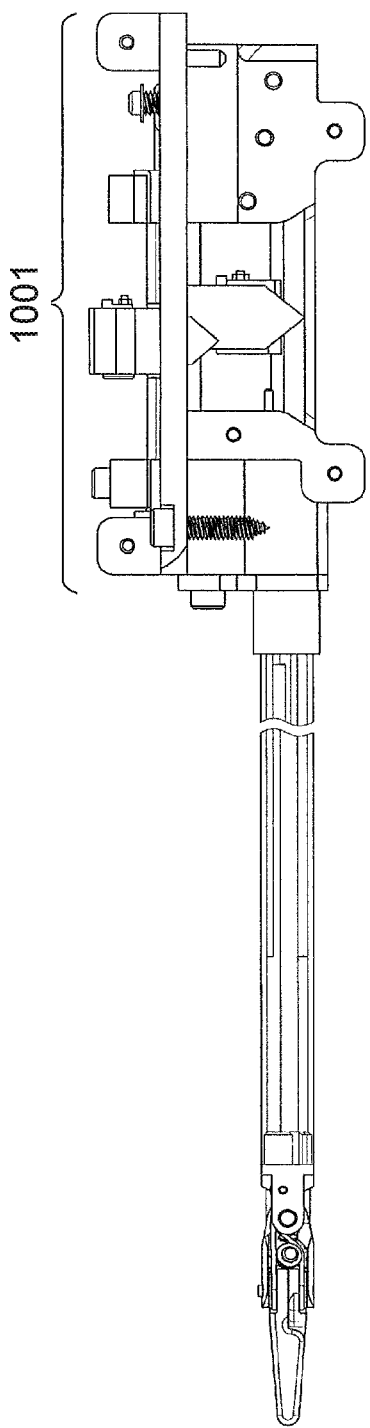

FIGS. 10a and 10b illustrate two views of the first, second and third pairs of driving elements extending from the articulation at the distal end of the instrument shaft to an exemplary instrument interface 1001. Mechanical drive from the robotic arm is transferred to the surgical instrument to articulate the joints of the instrument articulation via the instrument interface 1001 and a drive assembly interface located at the distal end of the robotic arm. To drive a joint of the instrument articulation, an interface element of the drive assembly interface is moved, which moves a mechanically engaged interface element of the instrument interface 1001. Movement of the instrument interface element moves a driving element, which drives a joint of the articulation.

Figure 11B:
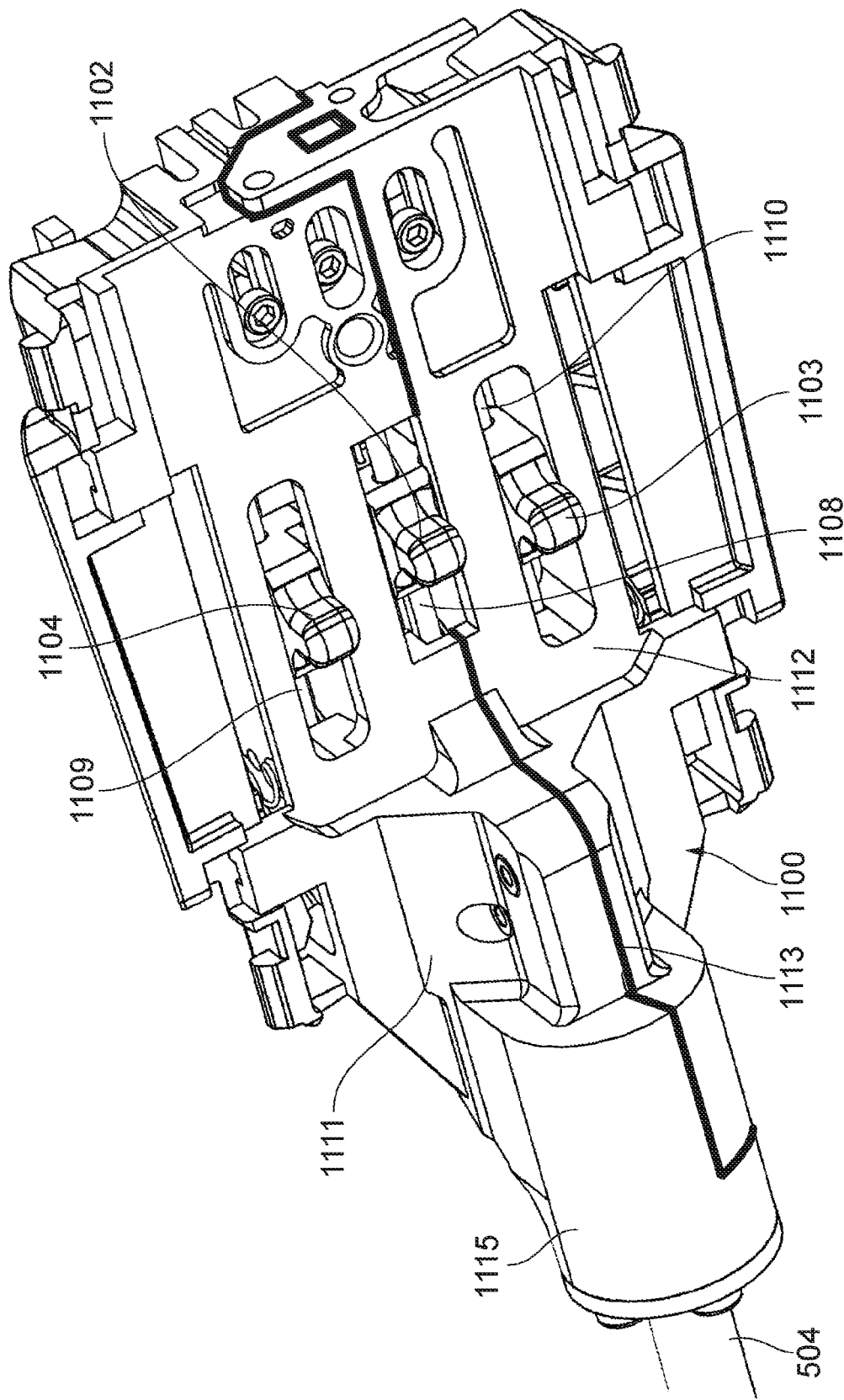

More detailed views of the instrument interface 1001 are illustrated in FIGS. 11a and 11b. FIG. 11a shows a view of the topside of the instrument interface, and FIG. 11b shows a view of the underside of the instrument interface.

The instrument interface 1001 comprises a chassis 1100 that supports a drive mechanism (denoted generally at 1101) for driving the joints of the instrument articulation. The drive mechanism comprises an arrangement of driving elements and pulleys which transfer drive provided by the robotic arm to the joints, as will be described in more detail below.

The instrument interface comprises three interface elements 1102, 1103 and 1104. The instrument interface elements form part of the instrument interface drive mechanism 1101. The first instrument interface element 1102 engages the first pair of driving elements A1,A2. The second instrument interface element 1103 engages the second pair of driving elements B1,B2. The third instrument interface element 1104 engages the third pair of driving elements C1,C2. Each driving element is secured to its associated instrument interface element. In other words, each driving element is fast with its associated instrument interface element. Each instrument interface element is displaceable relative to the chassis to cause a corresponding displacement of its engaged pair of driving elements.

Thus, in the examples illustrated in FIGS. 11a and 11b, each pair of driving elements engages a single instrument interface element in the instrument interface 1001. Each driving element engages an instrument interface element in the instrument interface. In other words, each driving element engages its own instrument interface element. A single instrument interface element drives a pair of driving elements. Each driving element pair is driven independently by a single instrument interface. In alternative arrangements, there may be a compound driving motion in which more than one instrument interface element drives a single driving element pair, a single instrument interface element drives more than one pair of driving elements, or a plurality of instrument interface elements collectively drive a plurality of driving elements.

The instrument interface elements 1102, 1103 and 1104 are dispersed across the width of the instrument interface. The instrument interface element 1102 is in this example aligned with the longitudinal axis 511 of the shaft 504. The other instrument interface elements 1103 and 1104 are located on either side of the aligned instrument interface element 1102. Specifically, each instrument interface element is constrained to travel along a respective linear path that is parallel to the longitudinal axis of the shaft, and instrument interface elements 1103 and 1104 are located on either side of a plane containing both the longitudinal axis of the shaft and the path of travel of the instrument interface element 1102. The instrument interface elements 1103 and 1104 are therefore not aligned with the longitudinal axis 511 of the shaft 504.

FIG. 11b shows an underside view of the instrument interface 1001. It can be seen that the undersides of the instrument interfaces are in the form of projections. The interface elements may project below the plane defined by the underside of the chassis 1100. Each instrument interface element 1102, 1103, 1104 is receivable in a corresponding socket of a drive assembly interface element. The shapes of the elements and socket may correspond such that when the drive assembly interface element is displaced, this displacement is transferred to the instrument interface element without any slippage. Thus, the body may fit snugly into the socket. The body may fit snugly into the socket at least along a dimension parallel to the displacement direction. In this way, a displacement of the socket causes a corresponding displacement of the body in the displacement direction. The instrument interface element may be displaceable over the same displacement range as its corresponding drive assembly interface element.

The drive mechanism 1101 further comprises sets of pulleys about which each pair of driving elements A1,A2; B1,B2 and C1,C2 are constrained to move within the instrument interface 1101. Specifically, the drive mechanism comprises a first set of pulleys 1105 about which the first pair of driving elements A1,A2 are constrained to move; a second set of pulleys 1106 about which the second pair of driving elements B1,B2 are constrained to move; and a third set of pulleys 1107 about which the third pair of driving elements C1,C2 are constrained to move. Each pulley of these sets of pulleys is supported by the chassis 1100. The pulleys may, for example, be rotatably mounted to the chassis.

The first set of pulleys 1105 lie on a central plane of the instrument interface. This central plane bisects the instrument interface along its longitudinal direction. The first set of pulleys therefore lie on a plane that is parallel to the longitudinal direction of the shaft 504. In the particular arrangement shown in FIG. 11a, the first set of pulleys 1105 lie on a plane that also contains the longitudinal axis 511 of the shaft, i.e. the first set of pulleys 1105 and the longitudinal axis 511 of the shaft are coplanar. It follows that the first set of driving elements A1,A2 lie on the same plane as the pulley set 1105, and thus are also coplanar with the longitudinal axis of the shaft.

The second and third sets of pulleys 1106 and 1107 lie on opposing sides of the central plane containing the first set of pulleys 1105.

The driving element pairs A1,A2; B1,B2 and C1,C2 extend out of the instrument interface 1001 at its distal end and into the proximal end of the shaft 504, through which they extend up to the joints of the instrument articulation. The chassis of the instrument interface comprises a mounting surface that the instrument shaft 504 is mounted to. The mounting surface is not directly visible in FIGS. 11a and 11b because it is covered by a congruent flange used to secure the instrument shaft 504. In this example, the mounting surface is an annulus, with the driving element pairs extending through the centre of the annulus. The mounting surface forms part of a mounting block 1115 located at the distal end of the chassis. The mounting block in this example has an outer profile that is cylindrical in shape. The mounting block may comprise a bore through which the driving element pairs extend.

Thus, to summarise, the instrument interface 1001 comprises a drive mechanism 1101 to transfer drive from a drive assembly of a robotic arm to the driving element pairs A1,A2, B1,B2 and C1,C2 to thereby drive the joints of the instrument articulation. Within the instrument interface, the pair of driving elements A1,A2 are constrained to move around the set of pulleys 1105 and engage with the first instrument interface element 1102. The pair of driving elements A1, A2 drive rotation of the articulation, and hence the end effector, about the first axis 510 (see FIG. 5a). The pair of driving elements B1, B2 are constrained to move around the set of pulleys 1106 and engage with the second instrument interface 1103. Driving elements B1,B2 drives rotation of the second joint 507. The pair of driving elements C1,C2 are constrained to move around the set of pulleys 1107 and engage with the third instrument interface 1104. Driving elements C1,C2 drives rotation of the third joint 513. Thus, each joint of the instrument articulation is driven by a respective pair of driving elements, and each pair of driving elements is in turn driven by a respective instrument interface element.

Each instrument interface element is displaceable within the instrument interface 1101 to drive its respective pair of driving elements. Since each instrument interface element is fast with a corresponding pair of driving elements, a displacement of the instrument interface element is transferred to a displacement of the pair of driving elements. Each instrument interface element may be displaceable along the same line as the line of the pair of driving elements that it is secured to. Each instrument interface element engages with a corresponding drive assembly interface element of the robot arm. Thus, displacement of the instrument interface element is driven by the robot arm. In this way, the robot arm drives the pairs of driving elements (and hence the joints of the instrument articulation).

In this example, each instrument interface element 1102, 1103 and 1104 is linearly displaceable within the instrument interface 1001. The interface elements may be displaceable along a displacement axis parallel to the longitudinal axis of the shaft 511. Each instrument interface element is mounted to a rail to support, or constrain, or guide, the motion of the interface element within the instrument interface. The rail may therefore be referred to as a guide bar. The rail/guide bar may be linear. As shown most clearly in FIG. 11b, the first instrument interface element 1102 is mounted to rail 1108; the second instrument interface element 1103 is mounted to rail 1109; and the third instrument interface element 1104 is mounted to rail 1110. The interface elements are slideably mounted to the rails to permit relative linear motion between the rail and the interface elements. That is, each interface element 1102, 1103, 1104 is slideable along its respective rail 1108, 1109, 1110. The rails are supported by, and fast with respect to, the chassis 1100. The guide rails may for example be mounted or secured to the chassis. The interface elements are therefore slideable relative to the chassis.

The chassis 1100 comprises a first chassis portion 1111 and a second chassis portion 1112. These chassis portions are secured together during assembly to form the chassis. The chassis is formed from the two chassis portions to aid the assembly of the driving elements and pulleys. For example, some of the driving elements and pulleys can be attached to a chassis portion before that portion is attached to the remaining chassis portion to form the chassis. Attaching at least some of the pulleys and driving elements before the chassis portions are combined can enable the driving elements and pulleys to be attached with more ease, particularly those that lie on the central plane of the chassis. In the present example, in which there are three pairs of driving elements and three sets of pulleys to attach, a convenient approach is to attach two sets of driving elements and their associated pulley sets to one of the chassis portions prior to joining the chassis portions together. The remaining pair of driving elements may be attached to the other chassis portion prior to joining the chassis portions, or afterwards.

The two chassis portions are secured together to form the chassis 1100. Each chassis portion is therefore a discrete component part of the chassis, i.e. the two chassis portions are not integrally formed together. As can be seen in FIGS. 11a and 11b, the chassis comprises a join 1113 along which the first chassis portion 1111 mates, or interfaces with, the second chassis portion 1112. The join 1113 therefore separates the first chassis portion 1111 from the second chassis portion 1112. In this regard, the join 1113 may be said to define the boundary separating the first and second chassis portions.

As shown in FIG. 11b, the join 1113 extends in a generally longitudinal direction of the chassis. The join 1113 may be said to extend along the longitudinal extent of the chassis, though, as shown in the example of FIG. 11b, the join need not be planar.

It can be seen from FIG. 11b that the join 1113 does not extend to the mounting surface to which the instrument shaft is mounted. That is, the distal-most point of the join is at a location proximal to the mounting surface. Specifically, the mounting block 1115 forms part of the first chassis portion 1111. The mounting block does not form part of the second chassis portion 1112.

The chassis 1100 is arranged so that the first set of driving elements A1,A2 are supported by the first chassis portion 1111. The third set of driving elements C1,C2 are also supported by the first chassis portion 1111. The second set of driving elements B1,B2 are supported by the second chassis portion 1112.

Other components of the drive mechanism 1101 are also distributed between the first and second chassis portions. For example, the first set of pulleys 1105 about which the first set of driving elements A1,A2 are constrained to move are supported by (e.g. rotatably mounted to) the first chassis portion 1111. Interface element 1102, which engages the driving element pair A1,A2, is also supported by the first chassis portion. For example, the guide bar 1108 on which the interface element is constrained to slide may be mounted to the first chassis portion, thereby making the interface element 1102 slideably mounted to the first chassis portion. Similarly, the pulley set 1107 about which driving element pair C1,C2 are constrained to move are supported by the first chassis portion 1111; and the interface element 1104, which engages the driving element pair C1,C2 is also supported by the first chassis portion. In contrast, the pulley set 1106 about which the driving element pair B1,B2 are constrained to move is supported by (e.g. rotatably mounted to) the second chassis portion 1112 that doesn't comprise the mounting surface. Interface element 1103, which engages the driving element pair B1,B2, is similarly supported by the second chassis portion 1112. For example, the guide bar 1110 on which the interface element is constrained to slide may be mounted to the second chassis portion, thereby making the interface element 1104 slideably mounted to the second chassis portion.

Figure 12:
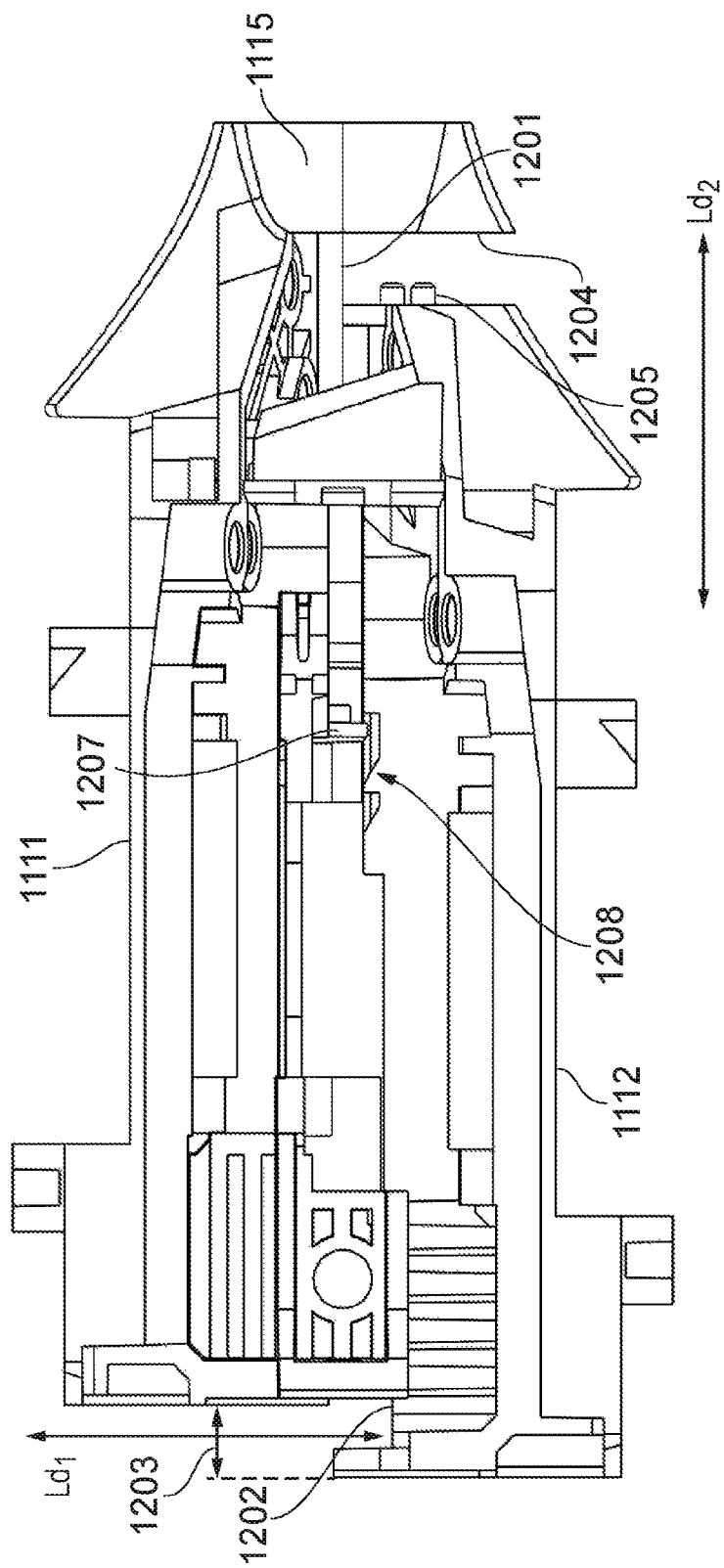
FIG. 12 shows a top view of two chassis portions forming part of the instrument interface in a laterally engaged configuration.
Figure 13:
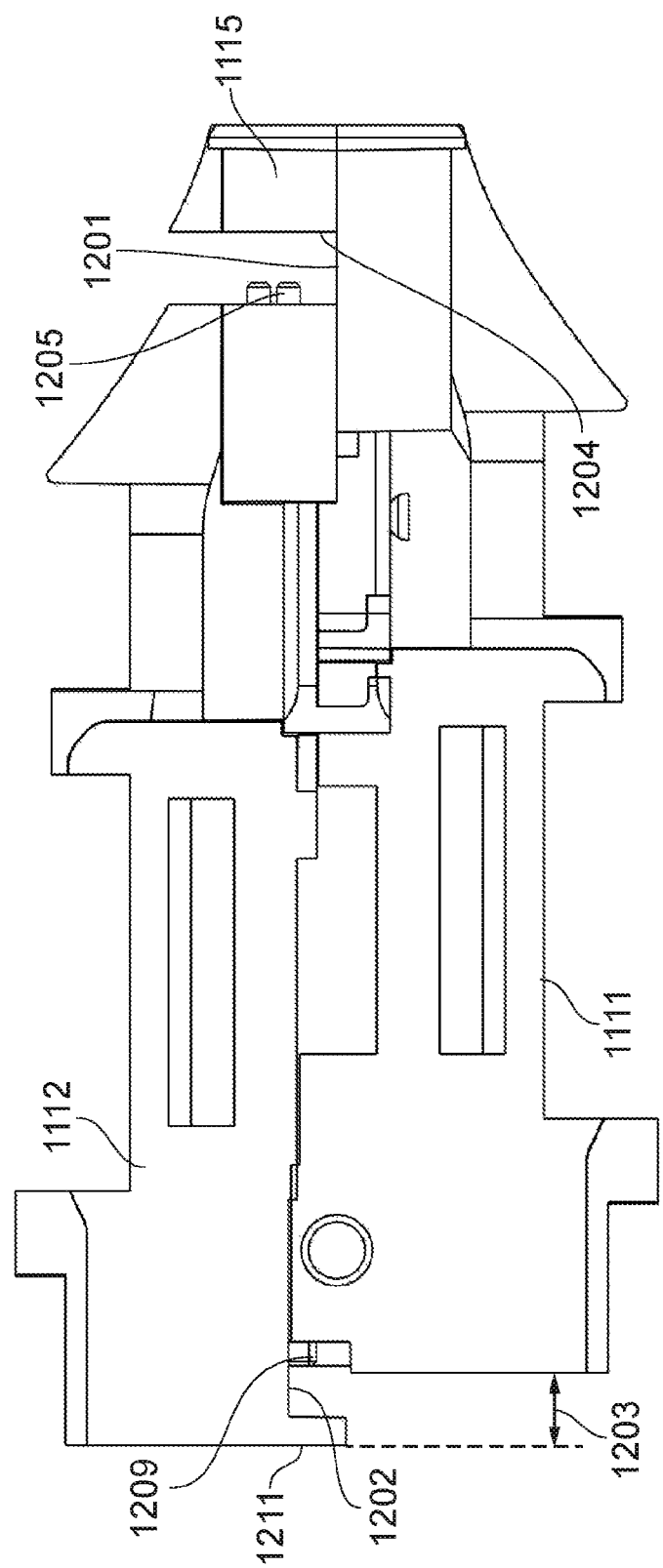
FIG. 13 shows a bottom view of the two chassis portions in the laterally engaged configuration.
Figure 14:
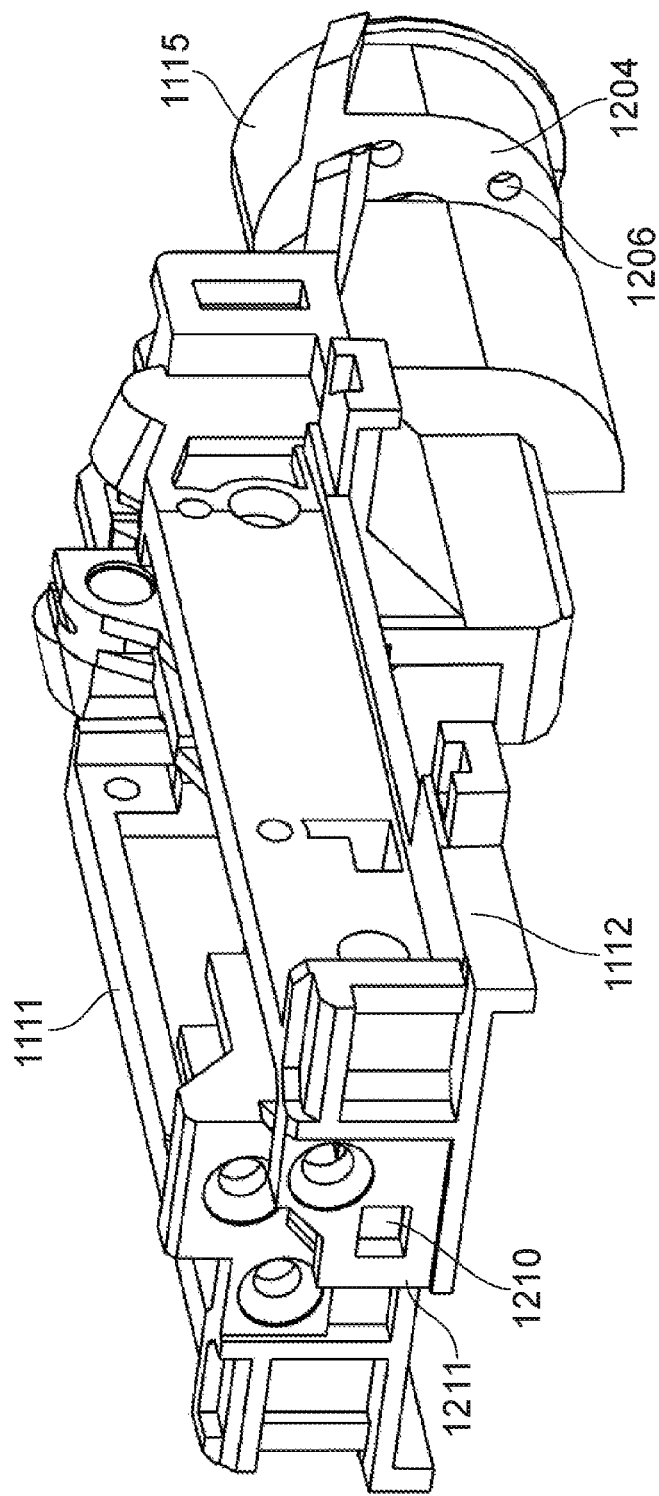
FIG. 14 shows a rear-quarter view of the two chassis portions in the laterally engaged configuration.
Figure 15:
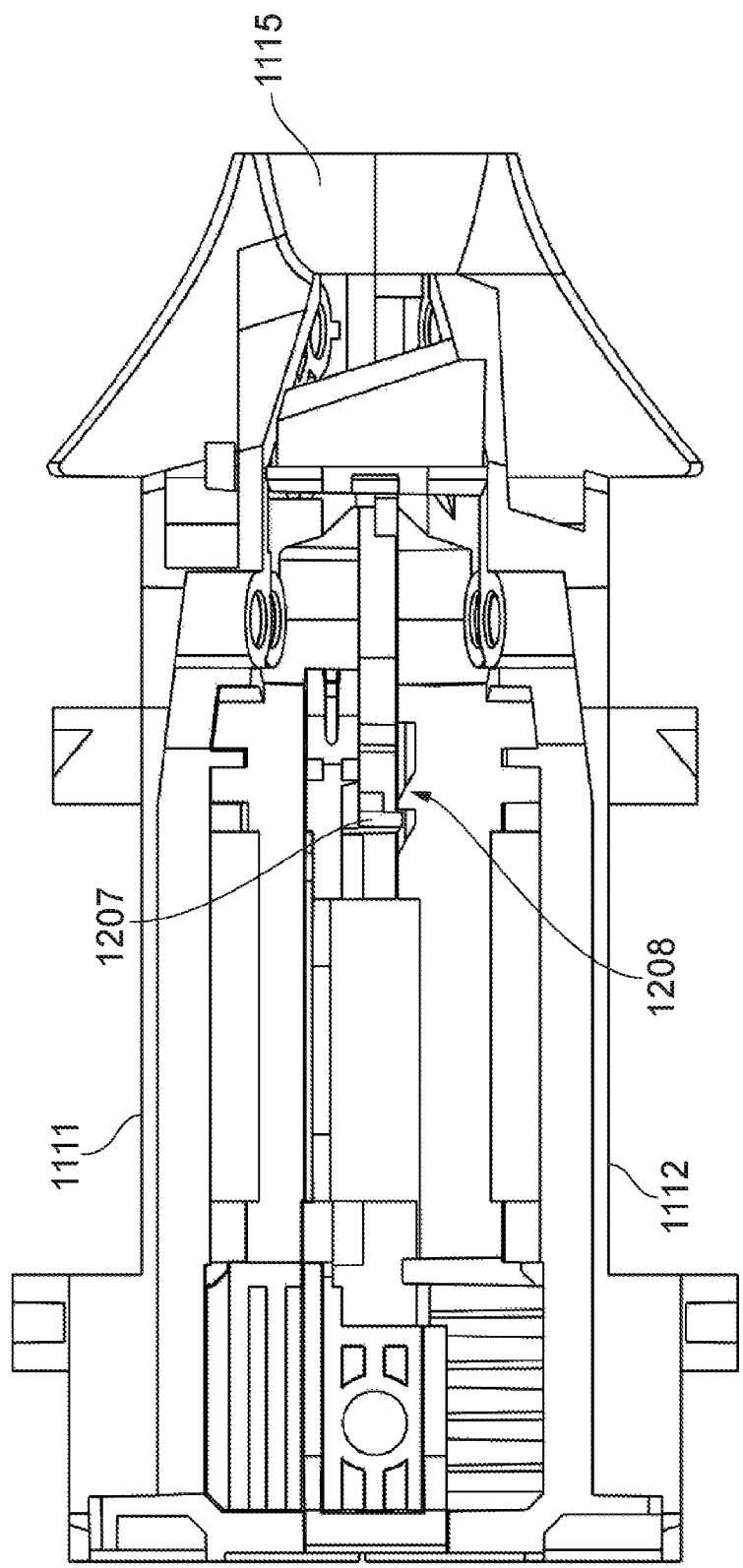
FIG. 15 shows a top view of the assembled chassis in which the two chassis portions are secured together.
Figure 16:
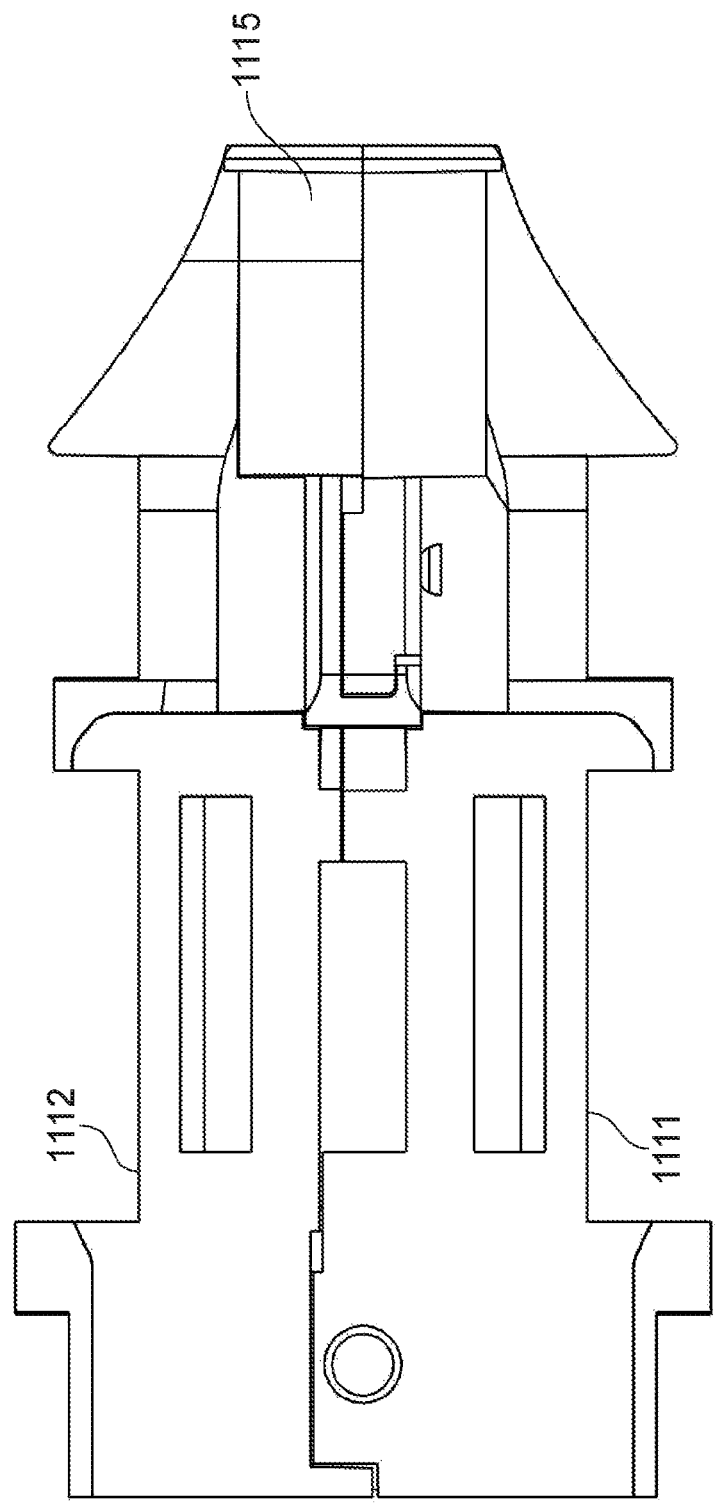
FIG. 16 shows a bottom view of the assembled chassis in which the two chassis portions are secured together.
Figure 17:
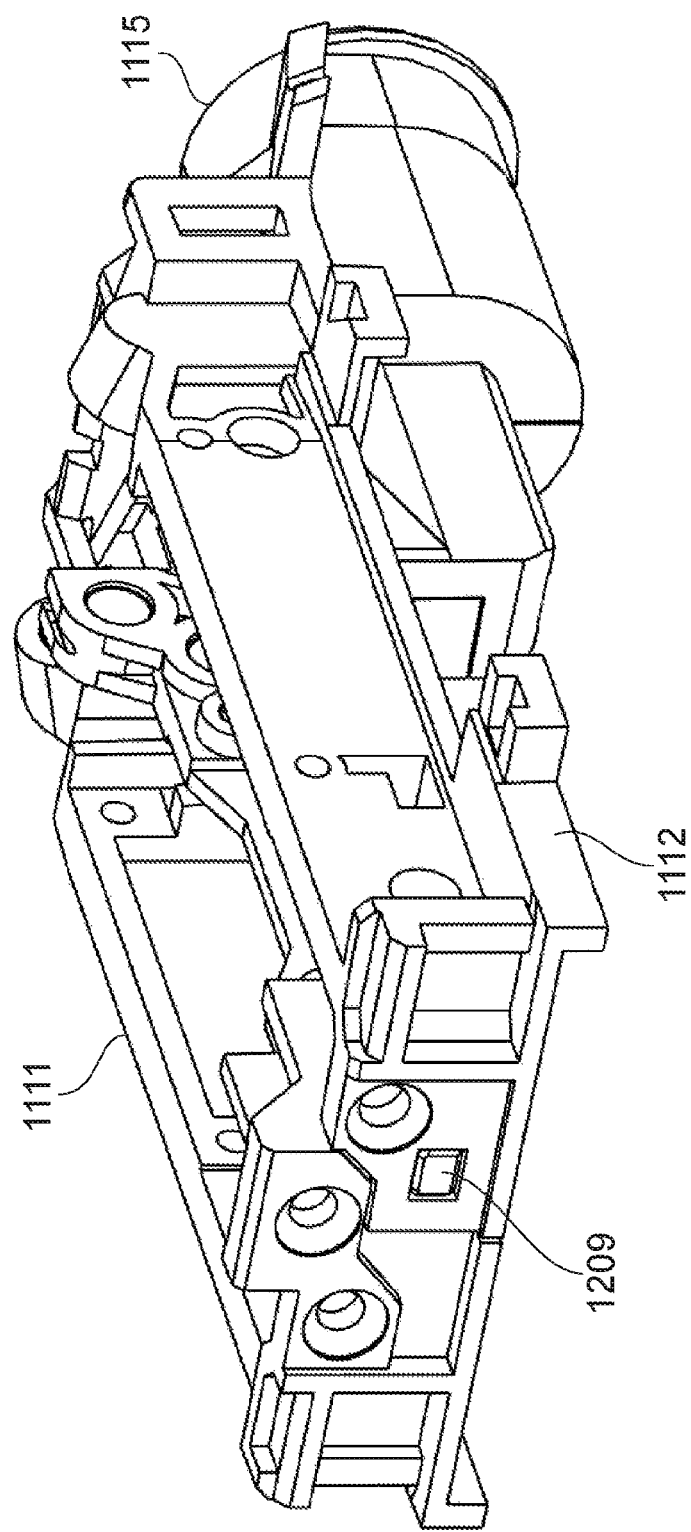
FIG. 17 shows a rear-quarter view of the assembled chassis in which the two chassis portions are secured together.

An example mechanism by which the chassis portions 1111 and 1112 are secured together will now be described with reference to FIGS. 12 to 17. FIGS. 12 to 14 show various views of the first and second chassis portions before assembly of the chassis is completed, and FIGS. 15 to 17 show corresponding views of the assembled chassis (i.e., when the first and second chassis portions are secured together). FIGS. 12 and 15 show a top view of the chassis; FIGS. 13 and 16 show a bottom view of the chassis; and FIGS. 14 and 17 show a rear-quarter view of the chassis. In each of these figures the components of the drive mechanism 1101 have been omitted for the purposes of clarity.

The chassis portions 1111 and 1112 are configured to be secured together by first being brought together laterally to a first position and then sliding the chassis portions relative to each other in a longitudinal direction parallel to the longitudinal axis of the shaft from the first position to a second position. That is, once brought together, the two chassis portions are slid relative to each other along a sliding axis parallel to the longitudinal axis of the shaft. This is shown most clearly in FIGS. 12 to 15. The lateral direction in which the two chassis portions may first be brought together is denoted $L_{d1}$. It will be appreciated that the portion 1111 may be moved laterally towards chassis portion 1112; chassis portion 1112 may be moved laterally towards chassis portion 1112; or the two chassis portions may be both be moved laterally towards each other. The longitudinal direction is denoted by the arrow $L_{d2}$. The lateral direction is transverse, or substantially transverse, to the longitudinal direction. In FIGS. 12, 13 and 14, the two chassis portions 1111 and 1112 have been brought together in the lateral direction $L_{d1}$ to a first position, but not yet slid relative to each other in the longitudinal direction $L_{d2}$ to the second position to secure the portions together.

The two chassis portions may be laterally engaged in the first position. In this example, each chassis portion comprises a lateral surface that interfaces with the lateral surface of the other chassis portion when the chassis portions are laterally brought together. The lateral surface for the chassis portion 1111 is labelled 1201, and the lateral surface for the chassis portion 1112 is labelled 1202 (shown in FIGS. 12 and 13). The chassis portions are brought together laterally so that the lateral surface 1201 interfaces, or mates with, the lateral surface 1202. Lateral surfaces 1201 and 1202 may therefore be referred to as internal lateral surfaces. Lateral surface 1201 may interface with lateral surface 1202 along it's depth, or height (i.e. in the direction perpendicular to the lateral and longitudinal directions).

The chassis portions are laterally brought together so that they are offset from each other in the longitudinal direction $L_{d2}$ in the first position. The chassis portions may be offset from each other relative to the position in which they are secured together. They may be offset from each other in the sense that the proximal (and distal) end of the chassis portion 1111 is offset in the longitudinal direction relative to the proximal (and distal) end of the chassis portion 1112. Put another way, the distal end of portion 1112 is proximal of the distal end of portion 1111, and the proximal end of portion 1111 is distal of the proximal end of portion 1112. In the examples shown in FIGS. 12 and 13, that offset is shown by the arrow 1203.

Once the chassis portions 1111 and 1112 have been laterally brought together, they are slid relative to each other in the longitudinal direction $L_{d2}$ to the second position to secure the portions together. The chassis portions are slid relative to each other so that the portions are brought together, or towards each other, in the longitudinal direction. Thus, chassis portion 1112 may be slid towards chassis portion 1111; chassis portion 1111 may be slid towards chassis portion 1112; or each chassis portion may be slid towards the other chassis portion. In each case, the distal end of chassis portion 1112 moves towards the distal end of portion 1111. In the particular arrangement shown in these figures, the chassis portions are slid relative to each other in the longitudinal direction to move the portion 1112 towards the proximal end of the shaft.

The chassis portions 1111 and 1112 are mutually shaped so that further sliding of portion 1112 relative to portion 1111 towards the proximal end of the shaft is prevented when the chassis portions are secured together in the second position. In other words, the second position is one end range of motion of the chassis portion 1112 relative to chassis portion 1111. The chassis portions are shaped so that a part of chassis portion 1112 abuts against a part of the portion 1111 when in the second position, preventing further movement of the portion 1112 relative to portion 1111 in the direction towards the proximal end of the shaft, In these examples, the part of chassis portion 1111 that abuts the chassis portion 1112 to prevent further longitudinal motion towards the proximal end of the shaft is mating surface 1204. The mating surface 1204 forms part of the mounting block 1115 to which the instrument shaft is mounted (the instrument shaft is not shown in FIGS. 12 to 17). A distal end of the chassis portion 1112 abuts the mating surface 1204 when the chassis portions are secured together. The mating surface 1204 therefore prevents further sliding of the chassis portion 1112 relative to the chassis portion 1111 in the longitudinal direction. Thus, before the chassis portions are slid relative to each other in the longitudinal direction, the distal end of the chassis portion 1112 is spaced apart from the mating surface 1204 in the longitudinal direction.

It has been appreciated that, by sliding the chassis portions towards each other in a longitudinal direction to secure the portions together, the tension in the driving elements functions to hold the chassis portions in place in the longitudinal direction. In other words, the tension in the driving elements opposes relative motion of the chassis portions away from each other in the longitudinal direction. For example, the pair of driving elements B1,B2 are secured relative to the chassis portion 1112. The driving elements B1,B2 are also attached to a pulley to drive joint 507 of the articulation 505 at the distal end of the shaft. Thus, the tension in the driving elements B1, B2 is in a generally longitudinal direction from the chassis to the articulation, and so operates to hold the distal end of the chassis portion 1112 in place against the mating surface 1204 of the chassis portion 1111. Thus, the approach of securing the chassis portions to each other described herein advantageously utilises the existing tension in the driving elements to enhance the strength with which the chassis portions are secured together.

The chassis may comprise a securing mechanism operable to secure the chassis portions together when the chassis portions are slid towards each other in the longitudinal direction $L_{d2}$. That is, sliding the chassis portions towards each other in the longitudinal direction may engage, or activate, the securing mechanism to secure the chassis portions together. Put another way, the chassis may comprise a securing mechanism that is activated or engaged by sliding the chassis portions towards each other in the longitudinal direction to secure the chassis portions together.

The securing mechanism may comprise securing elements that are operable to secure the chassis portions together when those portions are slid towards each other in the longitudinal direction. The example chassis portions 1111 and 1112 illustrated in FIGS. 12-17 comprise various examples of such securing elements, which will now be described.

As shown in FIGS. 12 and 13, the chassis portion 1112 comprises a set of protrusions (e.g. pins) 1205 at its distal end. These protrusions are arranged to mate with corresponding recesses 1206 (e.g. blind holes) in the mating surface 1204 when the chassis portions are slid towards each other in the longitudinal direction to the second position. The recesses are shown most clearly in FIG. 14.

The securing elements may alternatively or additionally take the form of latch parts. As best shown in FIGS. 12 and 15, the chassis portion 1111 comprises a latch part 1207 and the chassis portion 1112 comprises a corresponding latch part 1208. Latch parts 1207 and 1208 together form a latch. When the chassis portions are in a first position shown in FIGS. 12 to 14 (i.e. they are laterally engaged but not secured to each other), the latch is deactivated, or disengaged. Sliding the chassis portion 1112 towards the chassis portion 1111 in the longitudinal direction $L_{d2}$ engages the latch to secure the chassis portions to each other (as shown in FIG. 15). That is, the latch part 1207 and latch part 1208 engage each other.

A further example of the securing elements is the lug 1209 and corresponding opening 1210 (most clearly seen in FIGS. 13, 14 and 17). In particular, chassis portion 1111 comprises a lug at its proximal end (best seen in FIG. 13). The lug extends in a proximal direction away from the chassis portion. The chassis portion 1112 comprises a flange portion 1211 that comprises opening 1210. The opening may also be referred to as a window. When the chassis portions are in the first position the flange portion 1211 (and hence opening 1210) are proximal of the lug 1209. Thus, the lug and opening are disengaged. Sliding chassis portion 1112 towards the chassis portion 1111 in the longitudinal direction causes the lug to extend into the opening. That is, the lug engages the opening. The lug engages the opening to secure the chassis portions to each other.

In summary, the chassis portions are configured to be secured together by:
i.) Bringing the chassis portions together laterally to a first position. In this first position, the chassis portions are laterally engaged. For example, a lateral surface 1201 of the chassis portion 1111 may interface with a corresponding lateral surface 1202 of the chassis portion 1112. Also in this first position, the chassis portions are offset from each other in the longitudinal direction. The proximal ends of the chassis portions may be offset from each other in the longitudinal direction. The distal end of the chassis portion 1112 is longitudinally offset from the mating face 1204 of the chassis portion 1111. Put another way, the chassis portions are offset from each other relative to the position in which they are secured together. In the first position, the securing mechanism of the chassis is deactivated, or disengaged.
ii) Sliding the chassis portions towards each other in the longitudinal direction from the first position to a second position in which the chassis portions are secured together. There may be no longitudinal offset between the chassis portions in the second position. For example, the chassis portion 1112 may be slid relative to the chassis portion 1111 so that the distal end of the portion 1112 abuts a part of the chassis portion 1111. In the second position the proximal end of the chassis portions may be flush with each other. Also in the second position, the securing mechanism is activated, or engaged, to secure the chassis portions together. Conveniently, in the second position the tension in the driving elements routed around one or more pulleys mounted to the chassis portion 1112 holds that chassis portion against the chassis portion 1111 in the longitudinal direction.

The above examples described a mating surface 1204 that functions to prevent further relative motion of the chassis portions towards each other in the longitudinal direction when the chassis portions are secured together in the second position. In the described examples, the mating surface was described as perpendicular to the longitudinal direction. Though most effective at preventing further motion of the chassis portion 1112 in that orientation, in other implementations the mating surface may not be perpendicular to the longitudinal direction. It will also be appreciated that the component of the chassis portions used to limit the relative longitudinal motion may adopt different forms. For example, one of the chassis portions may instead comprise a flange, or a lip, or a step that engages the other chassis portion when the portions are secured together in the second position to prevent further relative longitudinal motion.

The above examples illustrate various securing elements that are activated to secure the chassis portions to each other as the chassis portions are slid towards each other in the longitudinal direction. It will be appreciated that the securing elements may take different forms. For example, the chassis portion 1111 may comprise a projection, or lug, and the chassis portion 1211 a slot that extends in the longitudinal direction. Sliding the portion 1112 towards portion 1111 in the longitudinal direction may then cause the lug to engage the slot to secure the chassis portions to each other. Alternatively, the chassis portion 1111 may comprise a ratchet track, and the chassis portion 1112 may comprise a pawl, or tooth, that is configured to engage the ratchet track to permit motion of the portion 1112 relative to the portion 1111 in one direction only. The ratchet track may take the form of a linear track of angled teeth. The pawl, or tooth, may engage the ratchet track as the chassis portion 1112 slides towards the chassis portion 1111 in the longitudinal direction. It will be appreciated that other types of securing elements are possible.

Though in the examples described above the securing mechanism includes three different types of securing elements, it will be appreciated that this is for the purpose of illustration only and that the securing mechanism may include one or more different types of securing elements.

In the examples described herein the drive assembly interface included three drive assembly interface elements that transferred drive to three instrument interface elements that transferred drive to three joints of the articulation at the distal end of the instrument shaft. It will be appreciated that the drive assembly interfaces described herein could be modified to include further or fewer drive assembly interface elements to transfer drive to further or fewer instrument interface elements. The instrument interfaces described herein could be modified to include further or fewer instrument interface elements to transfer drive to further or fewer joints of the articulation at the distal end of the instrument shaft. For example, the instrument interface could include two instrument interface elements that drive two driving element pairs only. One instrument interface may drive a driving element pair secured to one of the chassis portions, and the other instrument interface may drive a driving element pair secured to the other chassis portion. In other examples, the instrument interface may include a single interface element that drives a single driving element pair only. That driving element pair may be secured relative to one of the chassis portions only. he articulation itself could also be modified to include further or fewer joints.

It will also be appreciated that the end effector may only have one end effector element. In this case, the articulation does not include the third joint 513, the instrument interface does not include an instrument interface element for driving the third joint, and the drive assembly does not include a drive assembly interface element for driving that instrument interface element.

The chassis may be formed of more than two chassis portions. In this case, one of the chassis portions is configured to be secured to another one of the chassis portions by sliding those chassis portions towards each other along a longitudinal direction parallel to the shaft axis.

It will be appreciated that the shape and form of the join between the first and second chassis portions could take many different forms. The join illustrated in FIGS. 12a and 12b is merely an illustrative example of a join.

The instrument could be used for non-surgical purposes. For example, it could be used in a cosmetic procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A robotic surgical instrument, comprising:
a shaft;
an end effector element;
an articulation at a distal end of the shaft configured to articulate the end effector element, the articulation comprising a first joint permitting the end effector to adopt a range of configurations relative to the longitudinal axis of the shaft, the first joint being driveable by a first pair of driving elements; and
an instrument interface at a proximal end of the shaft, the instrument interface configured to connect the robotic surgical instrument with an interface at a distal end of a robotic arm, the instrument interface comprising:
a chassis formed from the securement of a first chassis portion to a second chassis portion, wherein the first pair of driving elements are secured relative to the chassis and are constrained to move about a first set of pulleys which are directly attached to the chassis, the chassis portions being configured to be secured together by sliding the chassis portions relative to each other in a longitudinal direction parallel to the longitudinal axis of the shaft.

2. A robotic surgical instrument as claimed in claim 1, wherein the chassis comprises a securing mechanism operable to secure the first chassis portion to the second chassis portion when the chassis portions are slid relative to each other in the longitudinal direction.

3. A robotic surgical instrument as claimed in claim 2, wherein the chassis portions are configured to be secured together by sliding the chassis portions relative to each other in the longitudinal direction from a first position in which the securing mechanism is disengaged, to a second position in which the securing mechanism is engaged to secure the chassis portions to each other.

4. A robotic surgical instrument as claimed in claim 2, wherein the securing mechanism comprises securing elements configured to engage when the chassis portions are slid towards each other in the longitudinal direction to thereby secure the chassis portions together.

5. A robotic surgical instrument as claimed in claim 1, wherein the first chassis portion comprises a mounting block to which the proximal end of the shaft is mounted.

6. A robotic surgical instrument as claimed in claim 1, wherein the chassis portions are configured to be secured together by sliding the chassis portions relative to each other to bring the second chassis portion towards the proximal end of the shaft.

7. A robotic surgical instrument as claimed in claim 1, wherein the chassis portions are mutually configured to prevent further sliding of the second chassis portion relative to the first chassis portion towards the proximal end of the shaft when the chassis portions are secured together.

8. A robotic surgical instrument as claimed in claim 1, wherein the first set of pulleys is rotatably secured to the second chassis portion so that tension in the first pair of driving elements holds the second chassis portion against the first chassis portion in the longitudinal direction when the chassis portions are secured together.

9. A robotic surgical instrument as claimed in claim 8, wherein the chassis portions are configured so that a part of the second chassis portion abuts against a part of the first chassis portion when the chassis portions are secured together to prevent further sliding of the second chassis portion relative to the first chassis portion in the longitudinal direction towards the proximal end of the shaft, the tension in the first pair of driving elements holding the part of the second chassis portion against the part of the first chassis portion.

10. A robotic surgical instrument as claimed in claim 9, wherein the part of the first chassis portion is a mating surface against which the second chassis portion abuts when the chassis portions are secured together.

11. A robotic surgical instrument as claimed in claim 10, wherein the mating surface is transverse to the longitudinal direction.

12. A robotic surgical instrument as claimed in claim 10, wherein the mating surface is integral with the mounting block.

13. A robotic surgical instrument as claimed in claim 1, wherein the first chassis portion and the second chassis portion each comprise a lateral interfacing surface, the chassis portions being configured to be secured together by laterally engaging the chassis portions by bringing the chassis portions together along a lateral direction so that the lateral interface surface of the first chassis portion interfaces the lateral interface surface of the second chassis portion, and thereafter sliding the chassis portions relative to each other in a longitudinal direction parallel to the longitudinal axis of the shaft.

14. A robotic surgical instrument as claimed in claim 10, wherein the chassis comprises a securing mechanism operable to secure the first chassis portion to the second chassis portion when the chassis portions are slid relative to each other in the longitudinal direction, the securing mechanism comprising a set of one or more protrusions located on a distal end of the second chassis portion and a corresponding set of one or more recesses located on the mating surface, the chassis being arranged so that the protrusions mate into the recesses when the second chassis portion is slid relative to the first chassis portion along the longitudinal direction.

15. A robotic surgical instrument as claimed in claim 2, wherein the securing mechanism comprises a first latch part located on the first chassis portion and a second latch part on the second chassis portion, the chassis being arranged so that the first latch part and the second latch part engage when the chassis portions are slid relative to the first chassis portion along the longitudinal direction.

16. A robotic surgical instrument as claimed in claim 2, wherein the securing mechanism comprises a lug located at the proximal end of the first chassis portion and an opening located at the proximal end of the second chassis portion, wherein the lug is configured to extend into the opening when the chassis portions are slid relative to the first chassis portion along the longitudinal direction.

17. A robotic surgical instrument as claimed in claim 1, wherein the first pair of driving elements are cables.

* * * * *